(12) United States Patent
Reid, Jr.

(10) Patent No.: US 9,925,005 B2
(45) Date of Patent: Mar. 27, 2018

(54) ABLATION SYSTEMS, PROBES, AND METHODS FOR REDUCING RADIATION FROM AN ABLATION PROBE INTO THE ENVIRONMENT

(71) Applicant: COVIDIEN LP, Mansfield, MA (US)

(72) Inventor: William O. Reid, Jr., Frederick, CO (US)

(73) Assignee: Covidien LP, Mansfiled, MA (US)

( * ) Notice: Subject to any disclaimer, the term of this patent is extended or adjusted under 35 U.S.C. 154(b) by 0 days.

(21) Appl. No.: 15/192,009

(22) Filed: Jun. 24, 2016

(65) Prior Publication Data

US 2016/0302863 A1   Oct. 20, 2016

Related U.S. Application Data

(62) Division of application No. 13/343,788, filed on Jan. 5, 2012, now Pat. No. 9,375,274.

(51) Int. Cl.
*A61B 18/18* (2006.01)
*A61B 90/00* (2016.01)
(Continued)

(52) U.S. Cl.
CPC ...... *A61B 18/1815* (2013.01); *A61B 18/1477* (2013.01); *A61B 18/18* (2013.01);
(Continued)

(58) Field of Classification Search
CPC . A61B 18/1815; A61B 90/04; A61B 18/1477; A61B 18/18; A61B 2090/0481;
(Continued)

(56) References Cited

U.S. PATENT DOCUMENTS

D223,367 S   4/1972   Kountz
D263,020 S   2/1982   Rau, III
(Continued)

FOREIGN PATENT DOCUMENTS

CN   1103807 A   6/1995
DE   390937 C   3/1924
(Continued)

OTHER PUBLICATIONS

International Search Report PCT/US03/22900 dated Dec. 2, 2003.
(Continued)

*Primary Examiner* — Carl H Layno
*Assistant Examiner* — Erin M Piateski

(57) ABSTRACT

The ablation systems, ablation probes, and corresponding methods according to the present disclosure reduce or eliminate energy radiating from an ablation probe into the environment. Some ablation probes include a retractable sheath that shields at least the radiating portion of the ablation probe. The retractable sheath and/or the ablation probe may include conduits through which a fluid may flow to shield the radiating portion and to drive the retractable sheath to an extended state. Other ablation probes include apertures defined in the probe walls through which the fluid can flow to expand a balloon surrounding the radiating portion. Yet other ablation probes include a thermal indicator to indicate the temperature of the ablation probe to a user. The ablation systems include fluid circuits and associated mechanical controls for varying the contents and/or flow rate of the fluid provided to the radiating portion of the ablation probe.

16 Claims, 11 Drawing Sheets

(51) Int. Cl.
*A61B 18/14* (2006.01)
*A61B 18/00* (2006.01)

(52) U.S. Cl.
CPC ..... *A61B 90/04* (2016.02); *A61B 2018/00011*
(2013.01); *A61B 2018/00017* (2013.01); *A61B
2018/00023* (2013.01); *A61B 2018/00077*
(2013.01); *A61B 2018/00196* (2013.01); *A61B
2018/00458* (2013.01); *A61B 2018/00577*
(2013.01); *A61B 2018/00791* (2013.01); *A61B
2018/00809* (2013.01); *A61B 2018/1425*
(2013.01); *A61B 2018/1475* (2013.01); *A61B
2018/1838* (2013.01); *A61B 2018/1869*
(2013.01); *A61B 2018/1892* (2013.01); *A61B
2090/0481* (2016.02)

(58) Field of Classification Search
CPC ........... A61B 2018/00011; A61B 2018/00017;
A61B 2018/00023; A61B 2018/00077;
A61B 2018/00196; A61B 2018/00458;
A61B 2018/00577; A61B 2018/00791
USPC .......................................................... 606/33
See application file for complete search history.

(56) References Cited

U.S. PATENT DOCUMENTS

| | | | |
|---|---|---|---|
| D266,842 S | 11/1982 | Villers et al. | |
| D278,306 S | 4/1985 | McIntosh | |
| D295,893 S | 5/1988 | Sharkany et al. | |
| D295,894 S | 5/1988 | Sharkany et al. | |
| 5,197,963 A | 3/1993 | Parins | |
| D354,218 S | 1/1995 | Van de Peer | |
| 5,380,321 A | 1/1995 | Yoon | |
| 5,419,325 A | 5/1995 | Dumoulin et al. | |
| 5,507,725 A * | 4/1996 | Savage | A61M 25/0147 604/95.04 |
| 5,871,525 A | 2/1999 | Edwards et al. | |
| D424,693 S | 5/2000 | Pruter | |
| D424,694 S | 5/2000 | Tetzlaff et al. | |
| D425,201 S | 5/2000 | Tetzlaff et al. | |
| 6,113,608 A * | 9/2000 | Monroe | A61F 2/966 604/264 |
| 6,241,702 B1 * | 6/2001 | Lundquist | A61M 25/0136 604/22 |
| D449,886 S | 10/2001 | Tetzlaff et al. | |
| D457,958 S | 5/2002 | Dycus et al. | |
| D457,959 S | 5/2002 | Tetzlaff et al. | |
| 6,409,724 B1 | 6/2002 | Penny et al. | |
| 6,485,413 B1 | 11/2002 | Boppart et al. | |
| D487,039 S | 2/2004 | Webster et al. | |
| D496,997 S | 10/2004 | Dycus et al. | |
| D499,181 S | 11/2004 | Dycus et al. | |
| 6,878,147 B2 | 4/2005 | Prakash et al. | |
| D525,361 S | 7/2006 | Hushka | |
| D531,311 S | 10/2006 | Guerra et al. | |
| 7,128,739 B2 | 10/2006 | Prakash et al. | |
| D533,942 S | 12/2006 | Kerr et al. | |
| D535,027 S | 1/2007 | James et al. | |
| D541,418 S | 4/2007 | Schechter et al. | |
| D541,938 S | 5/2007 | Kerr et al. | |
| 7,278,991 B2 | 10/2007 | Morris et al. | |
| D564,662 S | 3/2008 | Moses et al. | |
| D576,932 S | 9/2008 | Strehler | |
| D594,736 S | 6/2009 | Esjunin | |
| D594,737 S | 6/2009 | Kelly et al. | |
| D606,203 S | 12/2009 | Husheer et al. | |
| D613,412 S | 4/2010 | DeCarlo | |
| 7,862,559 B2 | 1/2011 | Prakash et al. | |
| D634,010 S | 3/2011 | DeCarlo | |
| 9,375,274 B2 | 6/2016 | Reid, Jr. | |
| 2002/0120261 A1 | 8/2002 | Morris et al. | |
| 2003/0109862 A1 | 6/2003 | Prakash et al. | |
| 2003/0195504 A1 | 10/2003 | Tallarida et al. | |
| 2005/0015081 A1 | 1/2005 | Turovskiy et al. | |
| 2005/0137662 A1 | 6/2005 | Morris et al. | |
| 2005/0222558 A1 | 10/2005 | Baxter et al. | |
| 2005/0267332 A1 * | 12/2005 | Paul | A61B 18/1492 600/127 |
| 2006/0106375 A1 | 5/2006 | Werneth et al. | |
| 2006/0282069 A1 | 12/2006 | Prakash et al. | |
| 2006/0293650 A1 | 12/2006 | Prakash et al. | |
| 2007/0100405 A1 | 5/2007 | Thompson et al. | |
| 2007/0112342 A1 | 5/2007 | Pearson et al. | |
| 2007/0197896 A1 | 8/2007 | Moll et al. | |
| 2007/0213809 A1 | 9/2007 | Weber | |
| 2008/0015664 A1 | 1/2008 | Podhajsky | |
| 2009/0131926 A1 | 5/2009 | Rusin et al. | |
| 2009/0222002 A1 | 9/2009 | Bonn et al. | |
| 2009/0295674 A1 * | 12/2009 | Bonn | A61B 18/18 343/872 |
| 2010/0057070 A1 | 3/2010 | Behnke et al. | |
| 2010/0082082 A1 | 4/2010 | Prakash et al. | |
| 2010/0249602 A1 * | 9/2010 | Buckley | A61B 8/12 600/467 |
| 2010/0305559 A1 | 12/2010 | Brannan et al. | |
| 2011/0004221 A1 | 1/2011 | Euteneuer et al. | |
| 2011/0077635 A1 | 3/2011 | Bonn | |
| 2011/0198327 A1 | 8/2011 | Prabhu | |
| 2011/0238053 A1 | 9/2011 | Brannan et al. | |

FOREIGN PATENT DOCUMENTS

| | | |
|---|---|---|
| DE | 1099658 B | 2/1961 |
| DE | 1139927 B | 11/1962 |
| DE | 1149832 B | 6/1963 |
| DE | 1439302 A1 | 1/1969 |
| DE | 2439587 A1 | 2/1975 |
| DE | 2455174 A1 | 5/1975 |
| DE | 2407559 A1 | 8/1975 |
| DE | 2415263 A1 | 10/1975 |
| DE | 2429021 A1 | 1/1976 |
| DE | 2460481 A1 | 6/1976 |
| DE | 2602517 A1 | 7/1976 |
| DE | 2504280 A1 | 8/1976 |
| DE | 2627679 A1 | 1/1977 |
| DE | 2540968 A1 | 3/1977 |
| DE | 2820908 A1 | 11/1978 |
| DE | 2803275 A1 | 8/1979 |
| DE | 2823291 A1 | 11/1979 |
| DE | 2946728 A1 | 5/1981 |
| DE | 3143421 A1 | 5/1982 |
| DE | 3045996 A1 | 7/1982 |
| DE | 3120102 A1 | 12/1982 |
| DE | 3510586 A1 | 10/1986 |
| DE | 3604823 A1 | 8/1987 |
| DE | 8712328 U1 | 2/1988 |
| DE | 3711511 C1 | 6/1988 |
| DE | 3904558 A1 | 8/1990 |
| DE | 3942998 A1 | 7/1991 |
| DE | 4238263 A1 | 5/1993 |
| DE | 4303882 A1 | 8/1994 |
| DE | 4339049 A1 | 5/1995 |
| DE | 29616210 U1 | 11/1996 |
| EP | 0556705 A1 | 8/1993 |
| EP | 0558429 A1 | 9/1993 |
| EP | 0648515 A1 | 4/1995 |
| EP | 0836868 A2 | 4/1998 |
| EP | 0882955 A1 | 12/1998 |
| EP | 1159926 A2 | 12/2001 |
| FR | 179607 | 11/1906 |
| FR | 1275415 A | 11/1961 |
| FR | 1347865 A | 1/1964 |
| FR | 2235669 A1 | 1/1975 |
| FR | 2276027 A1 | 1/1976 |
| FR | 2313708 A1 | 12/1976 |
| FR | 2502935 A1 | 10/1982 |
| FR | 2517953 A1 | 6/1983 |
| FR | 2573301 A1 | 5/1986 |
| FR | 2862813 A1 | 5/2005 |
| FR | 2864439 A1 | 7/2005 |
| JO | 08252263 | 10/1996 |
| JP | 55106 | 1/1993 |

(56) References Cited

FOREIGN PATENT DOCUMENTS

| JP | 0540112 | | 2/1993 |
|---|---|---|---|
| JP | 06343644 | | 12/1994 |
| JP | 07265328 | | 10/1995 |
| JP | 08056955 | | 3/1996 |
| JP | 09000492 | | 1/1997 |
| JP | 09010223 | | 1/1997 |
| JP | 11244298 | | 9/1999 |
| JP | 2000342599 | A | 12/2000 |
| JP | 2000350732 | A | 12/2000 |
| JP | 2001003776 | A | 1/2001 |
| JP | 2001008944 | A | 1/2001 |
| JP | 2001029356 | A | 2/2001 |
| JP | 2001037775 | A | 2/2001 |
| JP | 2001128990 | A | 5/2001 |
| JP | 2001231870 | A | 8/2001 |
| JP | 2008142467 | A | 6/2008 |
| SU | 166452 | | 11/1964 |
| SU | 401367 | A1 | 10/1973 |
| SU | 727201 | A2 | 4/1980 |
| WO | 2010035831 | A1 | 4/2010 |

OTHER PUBLICATIONS

International Search Report PCT/US03/37110 dated Jul. 25, 2005.
International Search Report PCT/US03/37111 dated Jul. 28, 2004.
International Search Report PCT/US03/37310 dated Aug. 13, 2004.
International Search Report PCT/US04/04685 dated Aug. 27, 2004.
International Search Report PCT/US04/13273 dated Dec. 15, 2004.
International Search Report PCT/US04/15311 dated Jan. 12, 2005.
International Search Report PCT/US05/36168 dated Aug. 28, 2006.
International Search Report PCT/US08/052460 dated Apr. 24, 2008.
International Search Report PCT/US09/31658 dated Mar. 11, 2009.
International Search Report PCT/US10/032796 dated Jul. 28, 2010.
B. Levy M.D., "Use of a New Vessel Ligation Device During Vaginal Hysterectomy" FIGO 2000, Washington, D.C.
B. F. Mullan et al., (May 1999) "Lung Nodules: Improved Wire for CT-Guided Localization," Radiology 211:561-565.
B. T. Heniford M.D. et al., "Initial Research and Clinical Results with an Electrothermal Bipolar Vessel Sealer" Oct. 1999.
Bergdahl et al., "Studies on Coagulation and the Development of an Automatic Computerized Bipolar Coagulator" Journal of Neurosurgery 75:1 (Jul. 1991), pp. 148-151.
Bulletin of the American Physical Society, vol. 47, No. 5, Aug. 2002, p. 41.
C. F. Gottlieb et al., "Interstitial Microwave Hyperthermia Applicators having Submillimetre Diameters", Int. J. Hyperthermia, vol. 6, No. 3, pp. 707-714, 1990.
C. H. Durney et al., "Antennas for Medical Applications", Antenna Handbook: Theory Application and Design, p. 24-40, Van Nostrand Reinhold, 1988 New York, V.T Lo, S.W. Lee.
Carbonell et al., "Comparison of the Gyms PlasmaKinetic Sealer and the Valleylab LigaSure.TM. Device in the Hemostasis of Small, Medium, and Large-Sized Arteries" Carolinas Laparoscopic and Advanced Surgery Program, Carolinas Medical Center,Charlotte, NC 2003.
Carus et al., "Initial Experience With the LigaSure.TM. Vessel Sealing System in Abdominal Surgery" Innovations That Work, Jun. 2002.
Chicharo et al., "A Sliding Goertzel Algorithm" Aug. 1996 DOS pp. 283-297 Signal Processing, Elsevier Science Publishers B.V. Amsterdam, NL, vol. 52, No. 3.
Chou, C.K., (1995) "Radiofrequency Hyperthermia in Cancer Therapy," Chapter 941n Biologic Effects of Nonionizing Electromagnetic Fields, CRC Press, Inc., pp. 1424-1428.
Chung et al., "Clinical Experience of Sutureless Closed Hemorrhoidectomy with LigaSure.TM." Diseases of the Colon & Rectum, vol. 46, No. 1, Jan. 2003.
Cosman et al., "Methods of Making Nervous System Lesions" in William RH, Rengachary SS (eds): Neurosurgery, New York: McGraw.cndot.Hill, vol. 111, (1984), pp. 2490-2499.

Cosman et al., "Radiofrequency Lesion Generation and its Effect on Tissue Impedance", Applied Neurophysiology, 51:230-242, 1988.
Cosman et al., "Theoretical Aspects of Radiofrequency Lesions in the Dorsal Root Entry Zone" Neurosurgery 15: (1984), pp. 945-950.
Crawford et al., "Use of the LigaSure.TM. Vessel Sealing System in Urologic Cancer Surger" Grand Rounds in Urology 1999, vol. 1, Issue 4, pp. 1 0-17.
Dulemba et al., "Use of a Bipolar Electrothermal Vessel Sealer in Laparoscopically Assisted Vaginal Hysterectomy" Sales/Product Literature; Jan. 2004.
E. David Crawford, "Evaluation of a New Vessel Sealing Device in Urologic Cancer Surgery" Sales/Product Literature 2000.
E. David Crawford, "Use of a Novel Vessel Sealing Technology in Management of the Dorsal Veinous Complex" Sales/Product Literature 2000.
Esterline, "Light Key Projection Keyboard" 2004 Advanced Input Systems, located at: <http://www.advanced-input.com/lightkey> last visited on Feb. 10, 2005.
Esterline Product Literature, "Light Key: Visualize a Virtual Keyboard. One With No Moving Parts", Nov. 1, 2003; 4 pages.
Geddes et al., "The Measurement of Physiologic Events by Electrical Impedence" Am. J. MI, Jan. Mar. 1964, pp. 16-27.
Goldberg et al., "Image-guided Radiofrequency Tumor Ablation: Challenges and Opportunities—Part I", (2001) J Vasc. Interv. Radiol, vol. 12, pp. 1021-1032.
Goldberg et al. (1995) "Saline-enhanced RF Ablation: Demonstration of Efficacy and Optimization of Parameters", Radiology, 197(P): 140 (Abstr).
Goldberg et al., "Tissue Ablation with Radiofrequency: Effect of Probe Size, Gauge, Duration, and Temperature on Lesion Volume" Acad Radio (1995) vol. 2, No. 5, pp. 399-404.
H. Schwarzmaier et al., "Magnetic Resonance Imaging of Microwave Induced Tissue Heating" Dept. of Laser Medicine & Dept. of Diagnostic Radiology; Heinrich-Heine-University, Duesseldorf, Germany; Dec. 8, 1994; pp. 729-731.
Heniford et al., "Initial Results with an Electrothermal Bipolar Vessel Sealer" Surgical Endoscopy (2001) 15:799-801.
Herman at al., "Laparoscopic Intestinal Resection With the LigaSure.TM. Vessel Sealing System: A Case Report" Innovations That Work, Feb. 2002.
Humphries Jr. et al., "Finite-Element Codes to Model Electrical Heating and Non-Linear Thermal Transport in Biological Media", Proc. ASME HTD-355, 131 (1997).
Ian D. McRury et al., The Effect of Ablation Sequence and Duration on Lesion Shape Using Rapidly Pulsed Radiofrequency Energy Through Electrodes, Feb. 2000, Springer Netherlands, vol. 4; No. 1, pp. 307-320.
Jarrett et al., "Use of the LigaSure.TM. Vessel Sealing System for Peri-Hilar Vessels in Laparoscopic Nephrectomy" Sales/Product Literature 2000.
Johnson et al., "Evaluation of a Bipolar Electrothermal Vessel Sealing Device in Hemorrhoidectomy" Sales/Product Literature, Jan. 2004.
Johnson, "Evaluation of the LigaSure.TM. Vessel Sealing System in Hemorrhoidectormy" American College of Surgeons (ACS) Clinic La Congress Poster (2000).
Johnson et al., "New Low-Profile Applicators for Local Heating of Tissues", IEEE Transactions on Biomedical Engineering, vol. BME-31, No. 1, Jan. 1984, pp. 28-37.
Johnson, "Use of the LigaSure.TM. Vessel Sealing System in Bloodless Hemorrhoidectomy" Innovations That Work, Mar. 2000.
Joseph G. Andriole M.D. et al., "Biopsy Needle Characteristics Assessed in the Laboratory", Radiology 148: 659-662, Sep. 1983.
Joseph Ortenberg, "LigaSure.TM. System Used in Laparoscopic 1st and 2nd Stage Orchiopexy" Innovations That Work, Nov. 2002.
K. Ogata, Modern Control Engineering, Prentice-Hall, Englewood Cliffs, N.J., 1970.
Kennedy et al., "High-burst-strength, feedback-controlled bipolar vessel sealing" Surgical Endoscopy (1998) 12: 876-878.
Kopans, D.B. et al., (Nov. 1985) "Spring Hookwire Breast Lesion Localizer: Use with Rigid-Compression. Mammographic Systems," Radiology 157(2):537-538.

(56) References Cited

OTHER PUBLICATIONS

Koyle et al., "Laparoscopic Palomo Varicocele Ligation in Children and Adolescents" Pediatric Endosurgery & Innovative Techniques, vol. 6, No. 1, 2002.
LigaSure.TM. Vessel Sealing System, the Seal of Confidence in General , Gynecologic, Urologic, and Laparaoscopic Surgery, Sales/Product Literature, Jan. 2004.
Livraghi et al., (1995) "Saline-enhanced RF Tissue Ablation in the Treatment of Liver Metastases", Radiology, p. 140 (Abstr).
Lyndon B. Johnson Space Center, Houston, Texas, "Compact Directional Microwave Antenna for Localized Heating," NASA Tech Briefs, Mar. 2008.
M. A. Astrahan, "A Localized Current Field Hyperthermia System for Use with 192-Iridium Interstitial Implants" Medical Physics. 9(3), May/Jun. 1982.
Magdy F. Iskander et al., "Design Optimization of Interstitial Antennas", IEEE Transactions on Biomedical Engineering, vol. 36, No. 2, Feb. 1989, pp. 238-246.
McGahan et al., (1995) "Percutaneous Ultrasound-guided Radiofrequency Electrocautery Ablation of Prostate Tissue in Dogs", Acad Radiol, vol. 2, No. 1: pp. 61-65.
McLellan et al., "Vessel Sealing for Hemostasis During Pelvic Surgery" Int'l Federation of Gynecology and Obstetrics FIGO World Congress 2000, Washington, DC.
MDTECH product literature (Dec. 1999) "FlexStrand": product description, 1 page.
MDTECH product literature (Mar. 2000) I'D Wire : product description, 1 page.
U.S. Appl. No. 12/977,415, filed Dec. 23, 2010, Joseph D. Brannan.
U.S. Appl. No. 12/985,124, filed Jan. 5, 2011, Joseph D. Brannan.
U.S. Appl. No. 12/985,136, filed Jan. 5, 2011, Joseph D. Brannan.
U.S. Appl. No. 12/985,155, filed Jan. 5, 2011, Joseph D. Brannan.
U.S. Appl. No. 12/985,179, filed Jan. 5, 2011, Joseph D. Brannan.
U.S. Appl. No. 13/020,562, filed Feb. 3, 2011, Joseph D. Brannan.
U.S. Appl. No. 13/020,664, filed Feb. 3, 2011, Kenlyn S. Bonn.
U.S. Appl. No. 13/024,041, filed Feb. 9, 2011, Joseph D. Brannan.
U.S. Appl. No. 13/029,521, filed Feb. 17, 2011, Joseph D. Brannan.
U.S. Appl. No. 13/029,594, filed Feb. 17, 2011, Joseph D. Brannan.
U.S. Appl. No. 13/043,665, filed Mar. 9, 2011, Richard A. Willyard.
U.S. Appl. No. 13/043,694, filed Mar. 9, 2011, Richard A. Willyard.
U.S. Appl. No. 13/050,729, filed Mar. 17, 2011, Casey M. Ladtkow.
U.S. Appl. No. 13/083,185, filed Apr. 8, 2011, Arnold V. DeCarlo.
U.S. Appl. No. 13/083,256, filed Apr. 8, 2011, Joseph D. Brannan.
U.S. Appl. No. 13/113,736, filed May 23, 2011, Ladtkow et al.
U.S. Appl. No. 13/118,929, filed May 31, 2011, Bonn et al.
U.S. Appl. No. 13/206,075, filed Aug. 9, 2011, Lee et al.
U.S. Appl. No. 13/236,997, filed Sep. 20, 2011, Behnke II, et al.
U.S. Appl. No. 13/237,068, filed Sep. 20, 2011, Behnke II, et al.
U.S. Appl. No. 13/237,187, filed Sep. 20, 2011, Behnke II, et al.
U.S. Appl. No. 13/237,342, filed Sep. 20, 2011, Behnke II, et al.
U.S. Appl. No. 13/237,488, filed Sep. 20, 2011, Behnke II, et al.
U.S. Appl. No. 13/267,369, filed Oct. 6, 2011, Prakash et al.
U.S. Appl. No. 13/268,143, filed Oct. 7, 2011, Kenlyn S. Bonn.
U.S. Appl. No. 13/281,605, filed Oct. 26, 2011, Prakash et al.
U.S. Appl. No. 13/290,462, filed Nov. 7, 2011, Kenlyn S. Bonn.
U.S. Appl. No. 13/298,461, filed Nov. 17, 2011, Buysse et al.
U.S. Appl. No. 13/344,753, filed Jan. 6, 2012, Lee et al.
U.S. Appl. No. 13/343,788, filed Jan. 5, 2012, William O. Reid, Jr.
U.S. Appl. No. 13/343,798, filed Jan. 5, 2012, William O. Reid, Jr.
U.S. Appl. No. 13/344,790, filed Jan. 6, 2012, Lee et al.
U.S. Appl. No. 13/351,463, filed Jan. 17, 2012, Smith et al.
U.S. Appl. No. 13/351,553, filed Jan. 17, 2012, Mahajan et al.
U.S. Appl. No. 13/358,129, filed Jan. 25, 2012, Joseph D. Brannan.
Alexander et al., "Magnetic Resonance Image-Directed Stereotactic Neurosurgery: Use of Image Fusion with Computerized Tomography to Enhance Spatial Accuracy" Journal Neurosurgery, 83 (1995), pp. 271-276.
Anderson et al., "A Numerical Study of Rapid Heating for High Temperature Radio Frequency Hyperthermia" International Journal of Bio-Medical Computing, 35 (1994), pp. 297-307.
Anonymous. (1999) Auto Suture MIBB Site Marker: Single Use Clip Applier, United States Surgical (Product instructions), 2 pages.
Anonymous. (2001) Disposable Chiba Biopsy Needles and Trays, Biopsy and Special Purpose Needles Cook Diagnostic and Interventional Products Catalog (products list), 4 pages.
Anonymous. (1987) Homer Mammalok.TM. Breast Lesion Needle/Wire Localizer, Namic.RTM. Angiographic Systems Division, Glens Falls, New York, (Hospital products price list), 4 pages.
Anonymous. (1999) MIBB Site Marker, United States Surgical (Sales brochure), 4 pages.
Anonymous. Blunt Tubes with Finished Ends. Pointed Cannula, Popper & Sons Biomedical Instrument Division, (Products Price List), one page, Jul. 19, 2000.
Anonymous. Ground Cannulae, ISPG, New Milford, CT, (Advertisement) one page, Jul. 19, 2000.
B. Levy M.D. et al., "Randomized Trial of Suture Versus Electrosurgical Bipolar Vessel Sealing in Vaginal Hysterectomy" Obstetrics & Gynecology, vol. 102, No. 1, Jul. 2003.
B. Levy M.D. et al., "Update on Hysterectomy New Technologies and Techniques" OBG Management, Feb. 2003.
European Search Report EP 07000885.9 dated May 15, 2007.
European Search Report EP 07001480.8 dated Apr. 19, 2007.
European Search Report EP 07001481.6 dated May 2, 2007.
European Search Report EP 07001485.7 dated May 23, 2007.
European Search Report EP 07001488.1 dated Jun. 5, 2007.
European Search Report EP 07001489.9 dated Dec. 20, 2007.
European Search Report EP 07001491 dated Jun. 6, 2007.
European Search Report EP 07001527.6 dated May 18, 2007.
European Search Report EP 07007783.9 dated Aug. 14, 2007.
European Search Report EP 07008207.8 dated Sep. 13, 2007.
European Search Report EP 07009026.1 dated Oct. 8, 2007.
European Search Report EP 07009028 dated Jul. 16, 2007.
European Search Report EP 07009029.5 dated Jul. 20, 2007.
European Search Report EP 07009321.6 dated Aug. 28, 2007.
European Search Report EP 07009322.4 dated Jan. 14, 2008.
European Search Report EP 07010672.9 dated Oct. 16, 2007.
European Search Report EP 07010673.7 dated Oct. 5, 2007.
European Search Report EP 07013779.9 dated Oct. 26, 2007.
European Search Report EP 07015191.5 dated Jan. 23, 2008.
European Search Report EP 07015601.3 dated Jan. 4, 2008.
European Search Report EP 07015602.1 dated Dec. 20, 2007.
European Search Report EP 07018375.1 dated Jan. 8, 2008.
European Search Report EP 07018821 dated Jan. 14, 2008.
European Search Report EP 07019173.9 dated Feb. 12, 2008.
European Search Report EP 07019174.7 dated Jan. 29, 2008.
European Search Report EP 07019178.8 dated Feb. 12, 2008.
European Search Report EP 07020283.3 dated Feb. 5, 2008.
European Search Report EP 07253835.8 dated Dec. 20, 2007.
European Search Report EP 08001016.8 dated Jan. 4, 2008.
European Search Report EP 08001019 dated Sep. 23, 2008.
European Search Report EP 08004974.5 dated Apr. 6, 2011.
European Search Report EP 08004975 dated Jul. 24, 2008.
European Search Report EP 08006731.7 dated Jul. 29, 2008.
European Search Report EP 08006733 dated Jul. 7, 2008.
European Search Report EP 08006734.1 dated Aug. 18, 2008.
European Search Report EP 08006735.8 dated Jan. 8, 2009.
European Search Report EP 08007924.7 partial dated Aug. 17, 2010.
European Search Report EP 08011282 dated Aug. 14, 2009.
European Search Report EP 08011705 dated Aug. 20, 2009.
European Search Report EP 08011705.4 extended dated Nov. 4, 2009.
European Search Report EP 08012829.1 dated Oct. 29, 2008.
European Search Report EP 08015842 dated Dec. 5, 2008.
European Search Report EP 08019920.1 dated Mar. 27, 2009.
European Search Report EP 08020530.5 dated May 27, 2009.
European Search Report EP 08169973.8 dated Apr. 6, 2009.
European Search Report EP 09010873.9 extended dated Nov. 13, 2009.
European Search Report EP 09010877.0 extended dated Dec. 3, 2009.
European Search Report EP 09012389.4 dated Jul. 6, 2010.
European Search Report EP 09151621 dated Jun. 18, 2009.

(56) References Cited

OTHER PUBLICATIONS

European Search Report EP 09156861.8 dated Aug. 4, 2009.
European Search Report EP 09161502.1 dated Sep. 2, 2009.
European Search Report EP 09161502.1 extended dated Oct. 30, 2009.
European Search Report EP 09165976.3 extended dated Mar. 17, 2010.
European Search Report EP 09166708 dated Oct. 15, 2009.
European Search Report EP 09166708.9 dated Mar. 18, 2010.
European Search Report EP 09169376.2 extended dated Dec. 16, 2009.
European Search Report EP 09172188.6 extended dated Apr. 23, 2010.
European Search Report EP 09172838.6 extended dated Jan. 20, 2010.
European Search Report EP 09173268.5 extended dated Jan. 27, 2010.
European Search Report EP 09704429.1 extended dated Mar. 23, 2011.
European Search Report EP 10001767.2 extended dated Jun. 18, 2010.
European Search Report EP 10004950.1 extended dated Jul. 2, 2010.
European Search Report EP 10004951.9 extended dated Jul. 2, 2010.
European Search Report EP 10005533.4 extended dated Sep. 24, 2010.
European Search Report EP 10005534.2 extended dated Sep. 17, 2010.
European Search Report EP 10006373.4 extended dated Nov. 11, 2010.
European Search Report EP 10008139.7 extended dated Nov. 30, 2010.
European Search Report EP 10008140.5 extended dated Dec. 28, 2010.
European Search Report EP 10008533.1 extended dated Dec. 20, 2010.
European Search Report EP 10008850.9 extended dated Nov. 30, 2010.
European Search Report EP 10009731.0 extended dated Jan. 28, 2011.
European Search Report EP 10009732.8 extended dated Jan. 26, 2011.
European Search Report EP 10010943.8 extended dated Feb. 1, 2011.
European Search Report EP 10011750.6 extended dated Feb. 1, 2011.
European Search Report EP 10014042.5 extended dated Feb. 18, 2011.
European Search Report EP 10014080.5 extended dated Mar. 17, 2011.
European Search Report EP 10014081.3 extended dated Mar. 17, 2011.
European Search Report EP 10014705.7 extended dated Apr. 27, 2011.
European Search Report EP 10158944.8 extended dated Jun. 21, 2010.
European Search Report EP 10161596.1 extended dated Jul. 28, 2010.
European Search Report EP 10161722.3 extended dated Jun. 16, 2010.
European Search Report EP 10163235.4 dated Aug. 10, 2010.
European Search Report EP 10172634.7 dated Nov. 9, 2010.
European Search Report EP 10185413.1 dated Dec. 7, 2010.
European Search Report EP 10185413.1 dated Mar. 14, 2011.
European Search Report EP 10191321.8 dated Apr. 7, 2011.
European Search Report EP 11000548.5 extended dated Apr. 14, 2011.
European Search Report EP 11004942 dated Sep. 23, 2011.
European Search Report EP 11174318.3 dated Nov. 7, 2011.
International Search Report PCT/US97/05066 dated Jun. 24, 1997.
International Search Report PCT/US98/18640 dated Jan. 29, 1999.
International Search Report PCT/US98/23950 dated Jan. 14, 1999.
International Search Report PCT/US99/24869 dated Feb. 11, 2000.
International Search Report PCT/US01/11218 dated Aug. 14, 2001.
International Search Report PCT/US01/11224 dated Nov. 13, 2001.
International Search Report PCT/US01/11340 dated Aug. 16, 2001.
International Search Report PCT/US01/11420 dated Oct. 16, 2001.
International Search Report PCT/US02/01890 dated Jul. 25, 2002.
International Search Report PCT/US02/11100 dated Jul. 16, 2002.
International Search Report PCT/US03/09483 dated Aug. 13, 2003.
European Search Report EP 04752343.6 dated Jul. 31, 2007.
European Search Report EP 04778192.7 dated Jul. 1, 2009.
European Search Report EP 05002027.0 dated May 12, 2005.
European Search Report EP 05002769.7 dated Jun. 19, 2006.
European Search Report EP 05013463.4 dated Oct. 7, 2005.
European Search Report EP 05013895 dated Oct. 21, 2005.
European Search Report EP 05014156.3 dated Jan. 4, 2006.
European Search Report EP 05016399 dated Jan. 13, 2006.
European Search Report EP 05017281 dated Nov. 24, 2005.
European Search Report EP 05019130.3 dated Oct. 27, 2005.
European Search Report EP 05019882 dated Feb. 16, 2006.
European Search Report EP 05020665.5 dated Feb. 27, 2006.
European Search Report EP 05020666.3 dated Feb. 27, 2006.
European Search Report EP 05021025.1 dated Mar. 13, 2006.
European Search Report EP 05021197.8 dated Feb. 20, 2006.
European Search Report EP 05021777 dated Feb. 23, 2006.
European Search Report EP 05021779.3 dated Feb. 2, 2006.
European Search Report EP 05021780.1 dated Feb. 23, 2006.
European Search Report EP 05021935 dated Jan. 27, 2006.
European Search Report EP 05021936.9 dated Feb. 6, 2006.
European Search Report EP 05021937.7 dated Jan. 23, 2006.
European Search Report EP 05021939 dated Jan. 27, 2006.
European Search Report EP 06006961 dated Oct. 22, 2007.
European Search Report EP 06006963 dated Aug. 4, 2006.
European Search Report EP 06008779.8 dated Jul. 13, 2006.
European Search Report EP 06009435 dated Jul. 13, 2006.
European Search Report EP 06010499.9 dated Jan. 29, 2008.
European Search Report EP 06014461.5 dated Oct. 31, 2006.
European Search Report EP 06018206.0 dated Oct. 20, 2006.
European Search Report EP 06019768 dated Jan. 17, 2007.
European Search Report EP 06020574.7 dated Oct. 2, 2007.
European Search Report EP 06020583.8 dated Feb. 7, 2007.
European Search Report EP 06020584.6 dated Feb. 1, 2007.
European Search Report EP 05021944.3 dated Jan. 25, 2006.
European Search Report EP 05022350.2 dated Jan. 30, 2006.
European Search Report EP 05023017.6 dated Feb. 24, 2006.
European Search Report EP 05025423.4 dated Jan. 19, 2007.
European Search Report EP 05025424 dated Jan. 30, 2007.
European Search Report EP 05810523 dated Jan. 29, 2009.
European Search Report EP 06000708.5 dated May 15, 2006.
European Search Report EP 06002279.5 dated Mar. 30, 2006.
European Search Report EP 06005185.1 dated May 10, 2006.
European Search Report EP 06005540 dated Sep. 24, 2007.
European Search Report EP 06006717.0 dated Aug. 11, 2006.
European Search Report EP 06020756.0 dated Feb. 16, 2007.
European Search Report EP 06022028.2 dated Feb. 13, 2007.
European Search Report EP 06023756.7 dated Feb. 21, 2008.
European Search Report EP 06024122.1 dated Apr. 16, 2007.
European Search Report EP 06024123.9 dated Mar. 6, 2007.
European Search Report EP 06025700.3 dated Apr. 12, 2007.
Medtrex Brochure "The O.R. Pro 300" 1 page, Sep. 1998.
Michael Choti, "Abdominoperineal Resection with the LigaSure.TM. Vessel Sealing System and LigaSure.TM. Atlas 20 cm Open Instrument" Innovations That Work, Jun. 2003.
Muller et al., "Extended Left Hemicolectomy Using the LigaSure.TM. Vessel Sealing System" Innovations That Work. LJ, Sep. 1999.
Murakami, R. et al., (1995). "Treatment of Hepatocellular Carcinoma: Value of Percutaneous Microwave Coagulation," American Journal of Radiology (AJR) 164:1159-1164.

(56) References Cited

OTHER PUBLICATIONS

Ni Wei et al., "A Signal Processing Method for the Coriolis Mass Flowmeter Based on a Normalized . . . " Journal of Applied Sciences—Ningyong Kexue Xuebao, Shangha CN, vol. 23, No. 2:(Mar. 2005); pp. 160-184.
Ogden, "Goertzel Alternative to the Fourier Transform" Jun. 1993 pp. 485-487 Electronics World; Reed Business Publishing, Sutton, Surrey, BG, vol. 99, No. 9, 1687.
Olsson M.D. et al., "Radical Cystectomy in Females" Current Surgical Techniques in Urology, vol. 14, Issue 3, 2001.
Organ, L W., "Electrophysiologic Principles of Radiofrequency Lesion Making" Appl. Neurophysiol, vol. 39: pp. 69-76 (1976/77).
P.R. Stauffer et al., "Interstitial Heating Technologies", Thennoradiotheray and Thermochemotherapy (1995) vol. I, Biology, Physiology, Physics, pp. 279-320.
Palazzo et al., "Randomized clinical trial of LigaSure.TM. versus open haemorrhoidectomy" British Journal of Surgery 2002,89,154-157 "Innovations in Electrosurgery" Sales/Product Literature; Dec. 31, 2000.
Paul G. Horgan, "A Novel Technique for Parenchymal Division During Hepatectomy" The American Journal of Surgery, vol. 181, No. 3, Apr. 2001, pp. 236-237.
Peterson et al., "Comparison of Healing Process Following Ligation with Sutures and Bipolar Vessel Sealing" Surgical Technology International (2001).
R. Gennari et al., (Jun. 2000) "Use of Technetium-99m-Labeled Colloid Albumin for Preoperative and Intraoperative Localization of Non palpable Breast Lesions," American College of Surgeons. 190(6):692-699.
Valleylab Brochure, "Reducing Needlestick Injuries in the Operating Room" 1 page, Mar. 2001.
Reidenbach, (1995) "First Experimental Results with Special Applicators for High-Frequency Interstitial Thermotherapy", Society Minimally Invasive Therapy, 4(Suppl 1):40 (Abstr).
Richard Wolf Medical Instruments Corp. Brochure, "Kleppinger Bipolar Forceps & Bipolar Generator" 3 pages, Jan. 1989.
Rothenberg et al., "Use of the LigaSure.TM. Vessel Sealing System in Minimally Invasive Surgery in Children" Int'l Pediatric Endosurgery Group (I PEG) 2000.
Sayfan et al., "Sutureless Closed Hemorrhoidectomy: A New Technique" Annals of Surgery, vol. 234, No. 1, Jul. 2001, pp. 21-24.
Sengupta et al., "Use of a Computer-Controlled Bipolar Diathermy System in Radical Prostatectomies and Other Open Urological Surgery" ANZ Journal of Surgery (2001) 71.9 pp. 538-540.
Sigel et al., "The Mechanism of Blood Vessel Closure by High Frequency Electrocoagulation" Surgery Gynecology & Obstetrics, Oct. 1965 pp. 823-831.
Solbiati et al., (2001) "Percutaneous Radio-frequency Ablation of Hepatic Metastases from Colorectal Cancer: Long-term Results in 117 Patients", Radiology, vol. 221, pp. 159-166.
Solbiati et al. (1995) "Percutaneous US-guided RF Tissue Ablation of Liver Metastases: Long-term Follow-up", Radiology, pp. 195-203.
Strasberg et al., "Use of a Bipolar Vassel-Sealing Device for Parenchymal Transection During Liver Surgery" Journal of Gastrointestinal Surgery, vol. 6, No. 4, Jul./Aug. 2002 pp. 569-574.
Stuart W. Young, Nuclear Magnetic Resonance Imaging—Basic Principles, Raven Press, New York, 1984.
Sugita et al., "Bipolar Coagulator with Automatic Thermocontrol" J. Neurosurg., vol. 41, Dec. 1944, pp. 777-779.
Sylvain Labonte et al., "Monopole Antennas for Microwave Catheter Ablation", IEEE Trans. on Microwave Theory and Techniques, vol. 44, No. 10, pp. 1832-1840, Oct. 1995.
T. Matsukawa et al., "Percutaneous Microwave Coagulation Therapy in Liver Tumors", Acta Radiologica, vol. 38, pp. 410-415, 1997.
T. Seki et al., (1994) "Ultrasonically Guided Percutaneous Microwave Coagulation Therapy for Small Hepatocellular Carcinoma," Cancer 74(3):817-825.
Urologix, Inc.-Medical Professionals: Targis.TM. Technology (Date Unknown). "Overcoming the Challenge" located at: <http://www.urologix.com!medicaUtechnology.html > Nov. 18, 1999; 3 pages.
Urrutia et al., (1988). "Retractable-Barb Needle for Breast Lesion Localization: Use in 60 Cases," Radiology 169 (3):845-847.
Valleylab Brochure, "Valleylab Electroshield Monitoring System" 2 pages, Nov. 1995.
ValleyLab Brochure, "Electosurgery: A Historical Overview", Innovations in Electrosurgery, 1999.
Vallfors et al., "Automatically Controlled Bipolar Electrocoagulation—'COA-COMP'" Neurosurgical Review 7:2-3 (1984) pp. 187-190.
W. Scott Helton, "LigaSure.TM. Vessel Sealing System: Revolutionary Hemostasis Product for General Surgery" Sales/Product Literature 1999.
Wald et al., "Accidental Burns", JAMA, Aug. 16, 1971, vol. 217, No. 7, pp. 916-921.
Walt Boyles, "Instrumentation Reference Book", 2002, Butterworth-Heinemann, pp. 262-264.
Wonnell et al., "Evaluation of Microwave and Radio Frequency Catheter Ablation in a Myocardium-Equivalent Phantom Model", IEEE Transactions on Biomedical Engineering, vol. 39, No. 10, Oct. 1992; pp. 1086-1095.
European Search Report EP 98300964.8 dated Dec. 13, 2000.
European Search Report EP 98944778 dated Nov. 7, 2000.
European Search Report EP 98958575.7 dated Oct. 29, 2002.
European Search Report EP 02786604.5 dated Feb. 10, 2010.
European Search Report EP 03721482 dated Feb. 6, 2006.
European Search Report EP 04009964 dated Jul. 28, 2004.
European Search Report EP 04013772 dated Apr. 11, 2005.
European Search Report EP 04015980 dated Nov. 3, 2004.
European Search Report EP 04015981.6 dated Oct. 25, 2004.
European Search Report EP 04027314 dated Mar. 31, 2005.
European Search Report EP 04027479 dated Mar. 17, 2005.
European Search Report EP 04027705 dated Feb. 10, 2005.
European Search Report EP 04710258 dated Oct. 15, 2004.
U.S. Appl. No. 08/136,098, filed Oct. 14, 1993, Roger A. Stem.
U.S. Appl. No. 08/483,742, filed Jun. 7, 1995, Roger A. Stem.
U.S. Appl. No. 12/861,333, filed Aug. 23, 2010, Joseph D. Brannan.
U.S. Appl. No. 12/944,951, filed Nov. 12, 2010, Joseph D. Brannan.
U.S. Appl. No. 12/977,390, filed Dec. 23, 2010, Joseph D. Brannan.

* cited by examiner

ABLATION SYSTEMS, PROBES, AND METHODS FOR REDUCING RADIATION FROM AN ABLATION PROBE INTO THE ENVIRONMENT

CROSS-REFERENCE TO RELATED APPLICATIONS

This application is a divisional application of U.S. patent application Ser. No. 13/343,788, now U.S. Pat. No. 9,375,274 filed Jan. 5, 2012, the entire contents of which are incorporated herein by reference.

BACKGROUND

1. Technical Field

The present disclosure generally relates to ablation systems. More particularly, the present disclosure is directed to ablation systems, probes, and methods for reducing or eliminating energy radiating from an ablation probe into a surgical environment.

2. Background of Related Art

In the treatment of diseases such as cancer, certain types of cancer cells have been found to denature at elevated temperatures (which are slightly lower than temperatures normally injurious to healthy cells.) These types of treatments, known generally as hyperthermia therapy, typically utilize electromagnetic radiation to heat diseased cells to temperatures above 41° C., while maintaining adjacent healthy cells at lower temperatures where irreversible cell destruction will not occur. Other procedures using electromagnetic radiation to heat tissue include ablation and coagulation. These procedures are typically done to denature or kill the targeted tissue.

Many medical procedures and devices that use electromagnetic radiation are known in the art. Some of these procedures and devices are used to treat tissue and organs, such as the prostate, heart, liver, lung, kidney, and breast. These medical procedures and devices can be broken down into two general categories: non-invasive and invasive.

Some non-invasive procedures involve treating tissue (e.g., a tumor) underlying the skin with microwave energy. The microwave energy non-invasively penetrates the skin to reach the underlying tissue. However, this non-invasive procedure may result in unwanted heating of healthy tissue. Thus, non-invasive procedures that use microwave energy require precise temperature control.

Some invasive procedures have been developed in which a microwave antenna probe is either inserted directly into a point of treatment via a normal body orifice or inserted percutaneously. These invasive procedures can provide better temperature control of the tissue being treated. Because of the small difference between the temperature required for denaturing malignant cells and the temperature injurious to healthy cells, a known heating pattern and predictable temperature control is important so that heating is confined to the tissue being treated. For instance, hyperthermia treatment at the threshold temperature of about 41.5° C. generally has little effect on most malignant growth of cells. However, at slightly elevated temperatures above the approximate range of 43° C. to 45° C., thermal damage to most types of normal cells is routinely observed. Accordingly, great care must be taken not to exceed these temperatures in healthy tissue.

To prevent damage to healthy tissue, the non-radiating portion of the ablation probe is cooled with a cooling solution having dielectric properties that are matched to the dielectric properties of the target tissue. When the ablation probe is removed from tissue, however, the probe still has the ability to efficiently radiate microwave energy because of the dielectric buffering provided by the cooling solution. Therefore, if the generator is still powering the probe after it is removed from tissue, individuals near the probe may be unnecessarily exposed to microwave energy.

SUMMARY

The ablation systems, ablation probes, and methods according to the present disclosure reduce or eliminate radiation from an ablation probe into the environment and require few or no changes to a generator.

In one aspect, the present disclosure features an ablation probe. The ablation probe includes a shaft and a retractable sheath. The distal portion of the shaft includes a radiating portion that delivers energy to tissue. The retractable sheath surrounds at least the radiating portion of the shaft. The retractable sheath prevents at least a portion of the energy from radiating outside of the retractable sheath and retracts as the shaft is inserted into tissue.

In some embodiments, the distal portion of the shaft includes a sharp tip and the retractable sheath includes a tip cover coupled to a distal end of the retractable sheath. The tip cover encloses the sharp tip when the retractable sheath is in an extended state. In some embodiments, the ablation probe includes a handle coupled to a proximal end of the shaft and the retractable sheath is coupled to a distal end of the handle.

In some embodiments, the retractable sheath is a compressible plastic cylinder and at least a portion of the compressible plastic cylinder is coated with an electrically conductive material. In other embodiments, the retractable sheath is a compressible, electrically conductive material formed in the shape of a cylinder. The compressible, electrically conductive material may be a metal, such as copper. In some embodiments, the retractable sheath is electrically coupled to an electrical ground.

In some embodiments, the retractable sheath includes at least one fluid conduit surrounding the shaft. For example, the retractable sheath may include an inner wall, an outer wall, and at least one fluid conduit disposed between these walls. The outer wall of the retractable sheath may be coated with an electrically conductive material.

In another aspect, the present disclosure features an ablation system. The ablation system includes an ablation probe, a fluid source, a fluid pump, and a generator. The ablation probe includes a shaft having a proximal portion and a distal portion. The distal portion of the shaft includes an antenna that delivers energy to tissue. The ablation probe also includes a sheath surrounding at least the radiating portion of the shaft. The sheath includes at least one fluid conduit defined within the sheath.

The fluid source of the ablation system is in fluid communication with the at least one fluid conduit of the sheath. The fluid pump, in turn, is in fluid communication with the fluid source and the at least one fluid conduit. The fluid pump pumps a fluid through the at least one fluid conduit. The generator electrically couples to the antenna and supplies electrical energy to the antenna.

In some embodiments, the fluid has dielectric properties that reduce the energy radiating from the radiating portion of the shaft. For example, the fluid may include air, a mixture of cooling fluid and air, or a mixture of cooling fluid and a dielectric material. In some embodiments, the energy delivered to tissue is microwave energy.

In some embodiments, the sheath is a retractable sheath that retracts when the shaft is inserted in tissue. In some embodiments, the fluid pump supplies a fluid to the at least one fluid conduit under a working pressure sufficient to extend the retractable sheath as the shaft is removed from tissue.

In yet another aspect, the present disclosure features a method of operating an ablation probe to reduce radiation of energy from the ablation probe to a surrounding surgical environment. The method includes retracting a sheath surrounding at least a radiating portion of an ablation probe. The sheath retracts along a longitudinal axis of the ablation probe toward a proximal end of the ablation probe as the radiating portion of the ablation probe is advanced towards a target volume of tissue. The method also includes advancing the sheath along the longitudinal axis of the ablation probe toward a distal end of the probe as the radiating portion of the ablation probe is removed from tissue such that the sheath surrounds at least the radiating portion of the ablation probe.

In some embodiments, the method further includes pumping a fluid into at least one fluid conduit disposed in the sheath. The fluid may have properties that at least reduce the energy radiating from the radiating portion of the ablation probe to the environment. The fluid may be nitrogen or air.

In the present disclosure, the term "proximal" refers to the portion of a structure that is closer to a user, while the term "distal" refers to the portion of the structure that is farther from the user.

BRIEF DESCRIPTION OF THE DRAWINGS

Various embodiments of the present disclosure are described herein with reference to the drawings wherein.

DETAILED DESCRIPTION

Particular embodiments of the present disclosure are described below with reference to the accompanying drawings.

Generally, the present disclosure relates to systems and corresponding methods for reducing or eliminating energy that radiates from ablation probes into the environment. These systems and corresponding methods require few or no changes to the electrosurgical generator that supplies power to the ablation probe. The systems include various shielding mechanisms for shielding individuals from unnecessary energy radiating from the ablation probe when it is removed from tissue.

The ablation systems according to the present disclosure include a retractable sheath or shield that shields at least the radiating portion of the ablation probe to reduce or eliminate the radiation of energy (e.g., microwave energy) into the environment. The retractable sheath may include conduits through which a shielding fluid flows to shield the radiating portion of the ablation probe. The shielding fluid may also be used to drive the retractable sheath from a retracted state to an extended state. In some embodiments, the ablation probe includes apertures formed in the walls of the ablation probe near the radiating portion and a balloon surrounding the ablation probe to cover the apertures. In these embodiments, the shielding fluid flows through the apertures into the balloon to expand the balloon surrounding the radiating portion.

The ablation systems also include fluid circuits having mechanical controls that vary the contents and/or flow rate of the shielding fluid that cools the radiating portion. For example, when the user operates (e.g., applies force to) the mechanical controls (e.g., the user uses his/her finger to depress a button), the cooling solution flows to the radiating portion. When the user again operates (e.g., removes force from) the mechanical controls (e.g., the user removes his/her finger from the button or depresses the button again), the shielding fluid or a mixture of the cooling solution and the shielding fluid is supplied to the radiating portion. The cooling solution may include cooled water or a water-based solution. The shielding fluid may also include a mixture of water and small particles of dielectric material.

Figure 1:
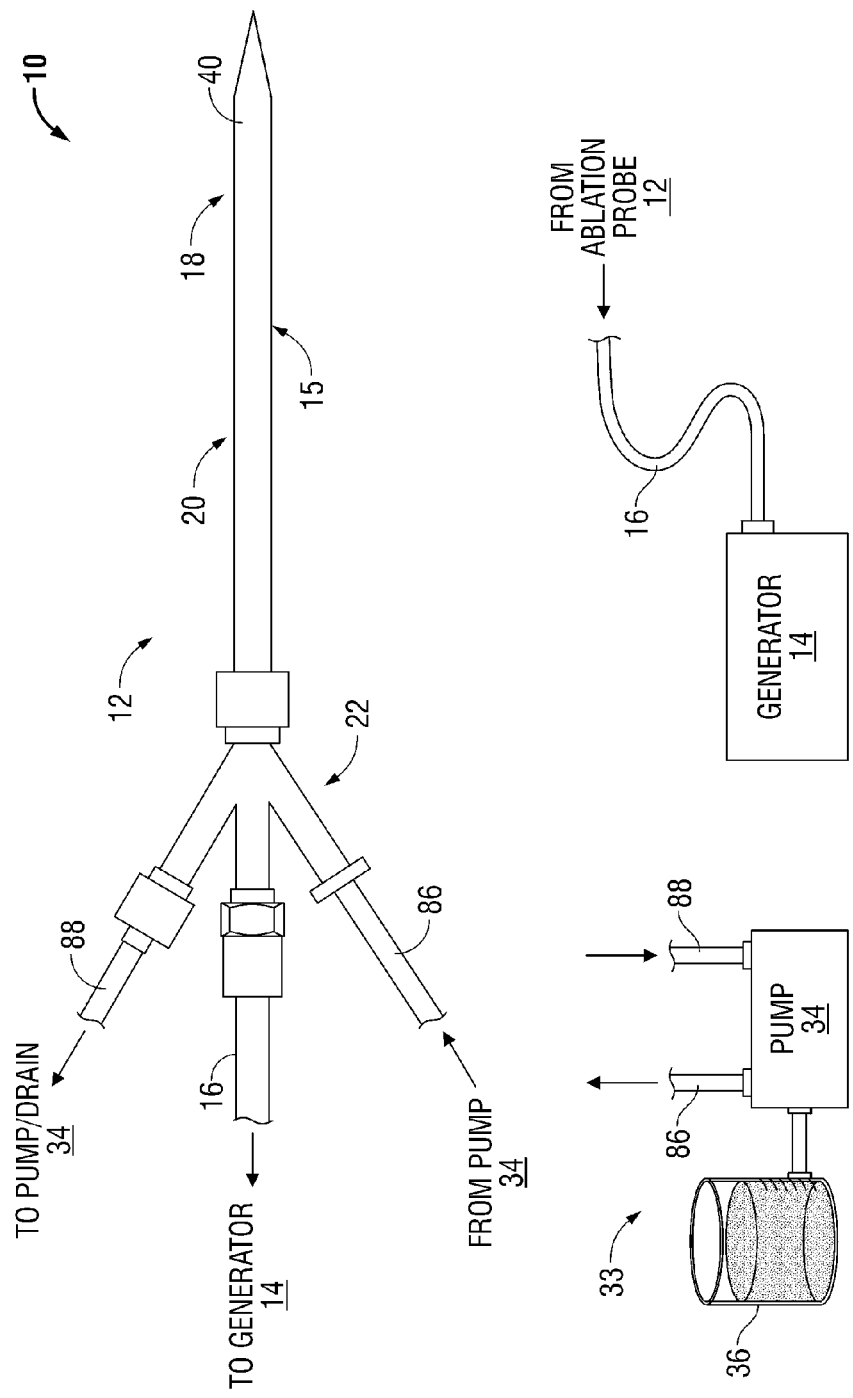
FIG. 1 is a diagram of a microwave ablation system according to embodiments of the present disclosure.

An ablation system according to embodiments of the present disclosure includes an ablation probe 12 having an antenna and/or an electrode that delivers energy to tissue. FIG. 1 illustrates an ablation system 10 including the ablation probe 12, a microwave generator 14, and a cooling fluid supply 33. The ablation probe 12 is coupled to the microwave generator 14 via a flexible coaxial cable 16. The ablation probe 12 is also fluidly coupled to the cooling fluid supply 33 via a fluid supply line or conduit 86 and a fluid return line or conduit 88. Cooling fluid leaves the ablation probe 12 through the fluid return line 88.

In a closed-loop cooling fluid system, the ablation probe 12 is fluidly coupled to the cooling fluid supply 33 via fluid return line 88 and cooling fluid is cycled through the cooling fluid supply 33. In an open-loop cooling fluid system, the cooling fluid flows through the fluid return line 88 to a drain or other suitable disposable receptacle and new cooling fluid is supplied to the cooling fluid supply 33 from a cooling fluid reservoir 36 or other suitable source of cooling fluid.

The ablation probe 12 generally includes a connection hub 22 and a shaft 15. The distal portion of the shaft 15 includes a radiating portion 18 and the proximal portion of the shaft 15 includes a feed line 20. The connection hub 22 connects the microwave generator 14 and the cooling fluid supply 33 to the ablation probe 12. The microwave signal is produced by the microwave generator 14, transmitted through the flexible coaxial cable 16, which connects to the connection hub 22, and the connection hub 22 facilitates the transfer of the microwave signal to the feed line 20. The connection hub 22 further facilitates the transfer of cooling fluid to and from the feed line 20. Cooling fluid, provided from the fluid pump 34 of the cooling fluid supply 33, is provided to the connection hub 22 through the fluid supply line 86. The connection hub 22 transfers the cooling fluid from the fluid supply line 86 to the cooling fluid supply lumen (not explicitly shown) of the feed line 20.

The cooling fluid, after being circulated through the feed line 20 and radiating portion 18 of the ablation probe 12, is returned to the connection hub 22 through the return lumen (not explicitly shown) of the feed line 20. Connection hub 22 facilitates the transfer of the cooling fluid from the return lumen (not explicitly shown) to the fluid return line 88.

In one embodiment, the microwave ablation system 10 includes a closed-loop cooling system wherein the fluid return line 88 returns the cooling fluid to the fluid pump 34 of the cooling fluid supply 33. The cooling fluid supply 33 cools the returned cooling fluid from the fluid return line 88 before recirculating at least a portion of the returned cooling fluid through the microwave ablation system 10.

In another embodiment, the fluid return line 88 connects to a suitable drain and/or reservoir (e.g., cooling fluid from the ablation probe 12 is not returned to the cooling fluid supply 33). Cooling fluid reservoir 36 of the cooling fluid supply 33 provides a continuous supply of cooling fluid to the fluid pump 34. Cooling fluid reservoir 36 may also include a temperature control system (not shown) configured to maintain the cooling fluid at a predetermined temperature. Coolant fluid may include any suitable liquid or gas, including air, or any combination of liquid and gas.

The ablation probe 12 may include any suitable microwave antenna 40 such as, for example, a dipole antenna, a monopole antenna and/or a helical antenna. The microwave generator 14 may be configured to provide any suitable electrical energy within an operational frequency from about 300 MHz to about 10 GHz. The physical length of the microwave antenna 40 is dependent on the frequency of the microwave energy signal generated by the microwave generator 14. For example, in one embodiment, a microwave generator 14 providing a microwave energy signal at about 915 MHz drives an ablation probe 12 that includes a microwave antenna 40 with a physical length of about 1.6 cm to about 4.0 cm.

Figure 2A:
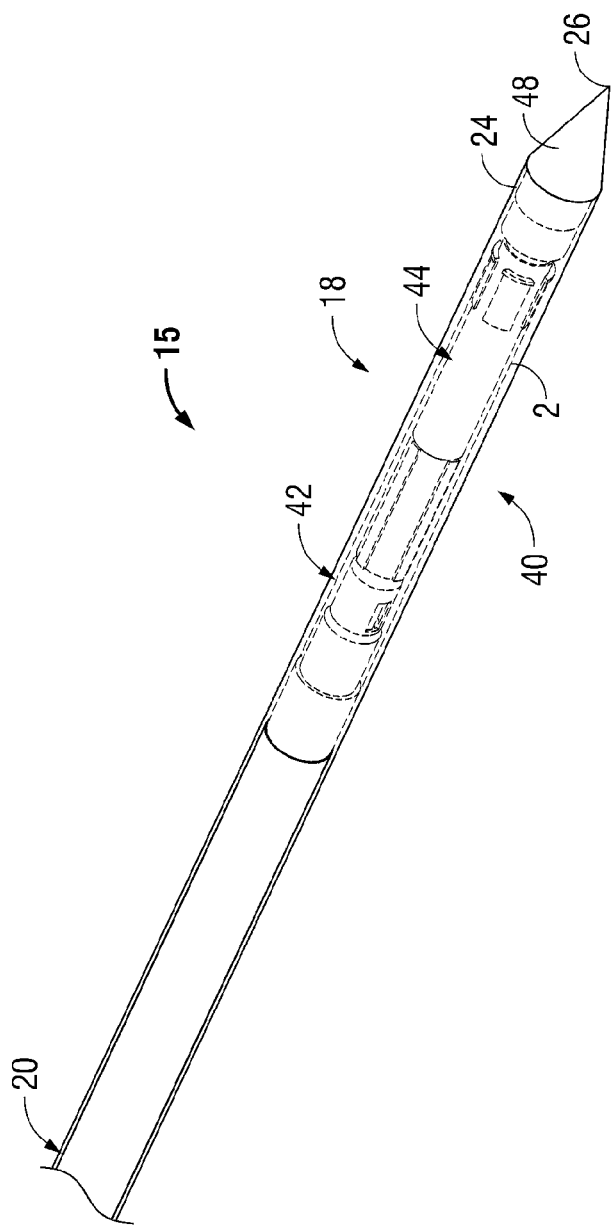
FIG. 2A is an perspective view of a distal portion of an ablation probe according to some embodiments of the present disclosure.

FIG. 2A is an enlarged view of the distal portion of the ablation probe 12 of FIG. 1 and includes a feed line 20, a proximal radiating portion 42 and a distal radiating portion 44. The proximal radiating portion 42 and the distal radiating portion 44 form a dipole antenna 40. As illustrated in FIG. 2A, the proximal radiating portion 42 and the distal radiating portion 44 are unequal thereby forming an unbalanced dipole antenna 40. The ablation probe 12 includes a sharp tip 48 having a tapered end 24 that terminates, in one embodiment, at a pointed tip 26 to allow for insertion into tissue with minimal resistance at a distal end of the radiating portion 18. In another embodiment, the radiating portion 18 is inserted into a pre-existing opening or catheter and the tip may be rounded or flat.

The sharp tip 48 may be machined from various stock rods to obtain a desired shape. The sharp tip 48 may be attached to the distal radiating portion 44 using various adhesives or bonding agents, such as an epoxy sealant. If the sharp tip 48 is metal, the sharp tip 48 may be soldered to the distal radiating portion 44 and may radiate electrosurgical energy. In another embodiment, the sharp tip 48 and a distal radiating portion 44 may be machined as one piece. The sharp tip 48 may be formed from a variety of heat-resistant materials suitable for penetrating tissue, such as ceramic, metals (e.g., stainless steel) and various thermoplastic materials, such as polyetherimide or polyimide thermoplastic resins, an example of which is Ultem® sold by General Electric Co. of Fairfield, Conn.

Figure 2B:
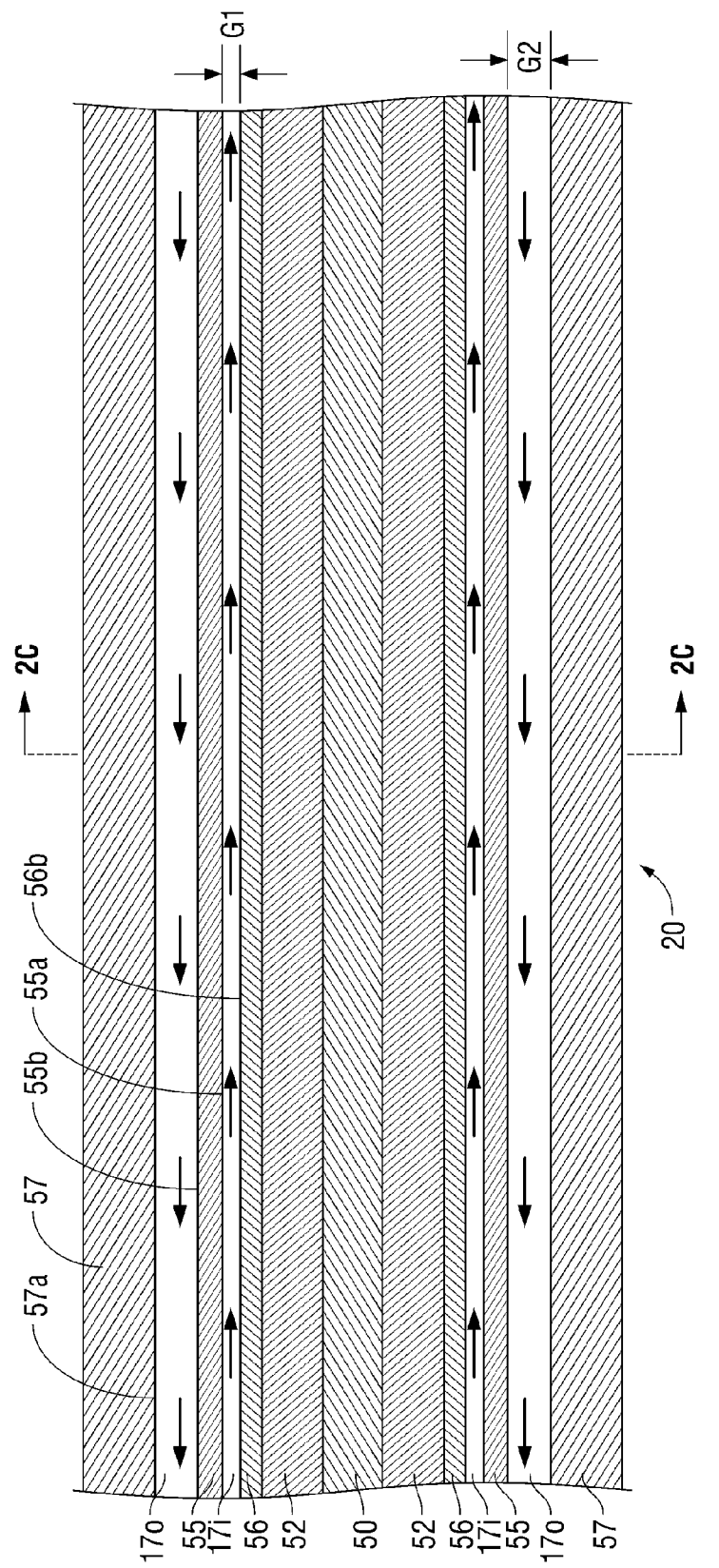
FIG. 2B is a longitudinal, cross-sectional view of a feed line portion of the ablation probe of FIG. 2A.
Figure 2C:
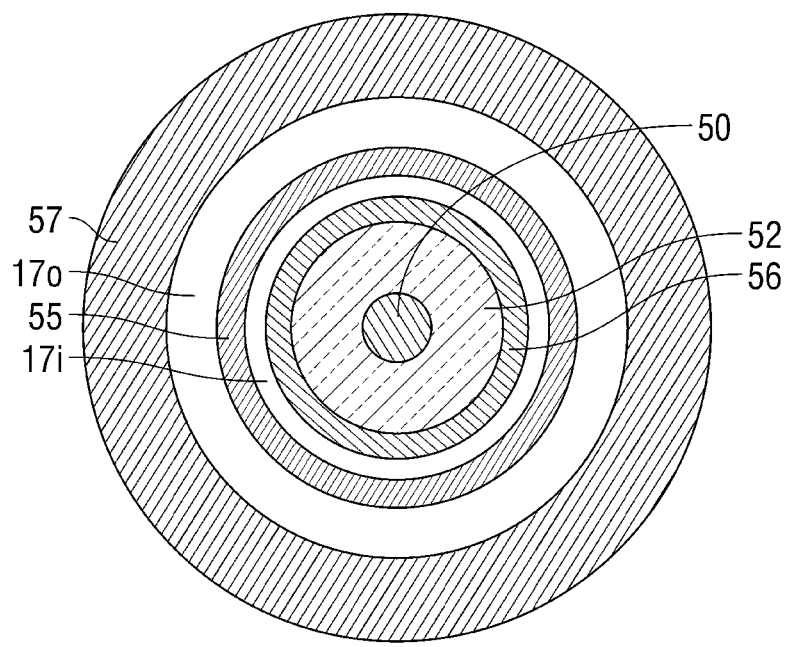
FIG. 2C is a transverse, cross-sectional view of the feed line portion of the ablation probe of FIG. 2A taken along the line 2C-2C of FIG. 2B.

FIG. 2B is a longitudinal cross-sectional view of a section of the feed line 20 of the ablation probe 12 of FIG. 1, and FIG. 2C is a transverse, cross-sectional view of the feed line 20 of the ablation probe 12 of FIG. 2B. Feed line 20 is coaxially formed with an inner conductor 50 at the radial center surrounded by a dielectric layer 52 and an outer conductor 56.

The inflow hypotube 55 is spaced apart and disposed radially outward from the outer conductor 56. The outer surface of the outer conductor 56b and the inner surface of the inflow hypotube 55a form an inflow channel 17i allowing cooling fluid to flow distally through the feed line 20 of the ablation probe 12 as indicated by the arrows within the inflow channel 17i. The inflow hypotube 55 may be formed from a variety of heat-resistant materials, such as ceramic, metals (e.g., stainless steel), various thermoplastic materials, such as polyetherimide or polyimide thermoplastic resins (e.g., Ultem®), or composite medical tubing, an example of which is PolyMed® sold by Polygon of Walkerton, Ind. In one embodiment, the inflow hypotube 55 may have a wall thickness less than about 0.010 inches. In another embodiment, the inflow hypotube 55 may have a wall thickness less than about 0.001 inches.

The outer hypotube 57 is spaced apart from, and radially outward from, the inflow hypotube 55. The outer surface of the inflow hypotube 55b and the inner surface of the outer hypotube 57a form an outflow channel 17o that allows cooling fluid to flow proximately through the feed line 20 of the ablation probe 12 as indicated by the arrows within the outflow channel 17o. The outer hypotube 57 may be formed from a variety of heat-resistant materials, such as ceramic, metals (e.g., stainless steel), various thermoplastic materials, such as polyetherimide, polyimide thermoplastic resins (e.g., Ultem®), or composite medical tubing (e.g., PolyMed®). In one embodiment, the outer hypotube 57 may have a wall thickness less than about 0.010 inches. In another embodiment, the outer hypotube 57 may have a wall thickness less than about 0.001 inches.

The substantially radially concentric cross-sectional profile of the feed line, as illustrated in FIG. 2C, provides uniform flow of fluid in both the inflow channel 17i and the outflow channel 17o. For example, an inflow channel gap G1 defined between the outer surface of the outer conductor 56b and the inner surface of the inflow hypotube 55a is substantially uniform around the circumference of the outer conductor 56. Similarly, an outflow channel gap G2 defined between the outer surface of the inflow hypotube 55*b* and the inner surface of the outer hypotube 57 is substantially uniform around the circumference of the inflow hypotube 55.

In addition, the cross-sectional area of the inflow channel 17*i* and the outflow channel 17*o* (i.e., the effective area of each channel in which fluid flows) is the difference between the area at the outer surface of the inflow channel 17*i* and the outflow channel 17*o* (i.e., the area at the inner diameter of the inflow hypotube 55 and the area at the inner diameter of the outer hypotube 57, respectively) and the area at the inner surface of the inflow channel 17*i* and the outflow channel 17*o* (i.e., the area at the outer diameter of the outer conductor 56 and the area at the outer diameter of the inflow hypotube 55). The cross-sectional area of the inflow channel 17*i* and the outflow channel 17*o* is substantially uniform along the longitudinal length of the feed line 20. In addition, transverse shifting of the inflow hypotube 55 within the outer hypotube 57 or transverse shifting of the outer conductor 56 within the inflow hypotube 55, may create a non-uniform inflow or outflow channel gap G1, G2, but will not affect the cross-sectional area of either the inflow channel 17*i* and/or the outflow channel 17*o*.

Figure 2D:
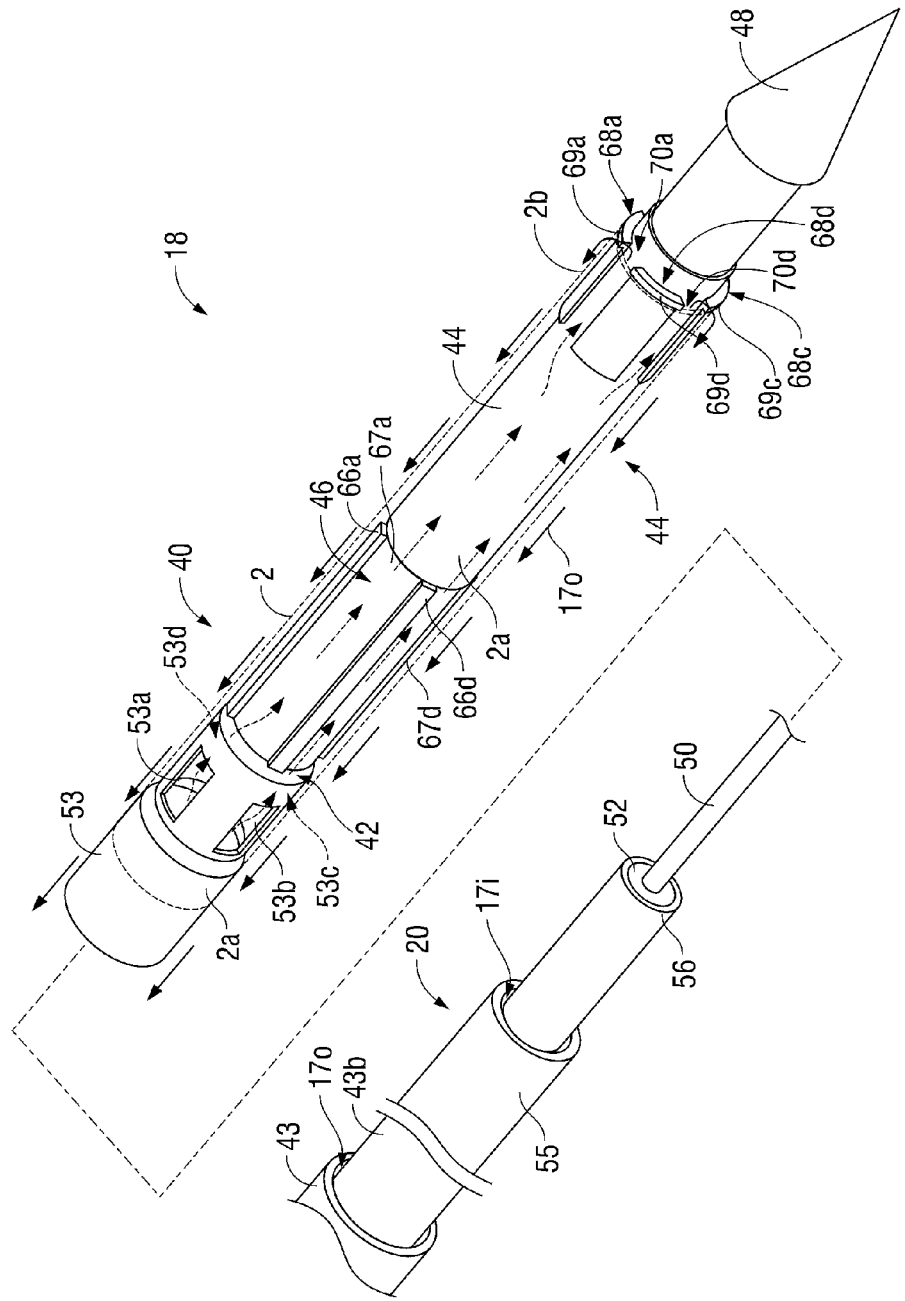
FIG. 2D is an internal perspective view of the distal portion of the ablation probe of FIG. 2A illustrating the coaxial inflow and outflow channels.

FIG. 2D, which is a perspective view of the radiating portion 18 of FIG. 1, illustrates the inflow fluid flow pathways. The radiating portion 18 is formed by inserting the distal portion of the feed line 20 into the microwave antenna 40.

The feed line 20 is configured to provide cooling fluid and a microwave energy signal to the microwave antenna 40. As discussed hereinabove, the feed line 20 provides cooling fluid through the inflow channel 17*i* formed between the inflow hypotube 55 and the outer conductor 56 of the feed line 20. The feed line 20 also provides a microwave energy signal between the inner conductor 50 and the outer conductor 56.

The antenna 40 includes a tapered inflow transition collar 53, a channeled puck 46, a distal radiating portion 44, including a plurality of antenna sleeve stops 68*a*-68*d*, and a sharp tip 48. The feed line 20, when inserted into the antenna 40, connects the outer conductor 56 to the tapered inflow transition collar 53 and the inner conductor 50 to the distal radiating portion 44.

Figure 3:
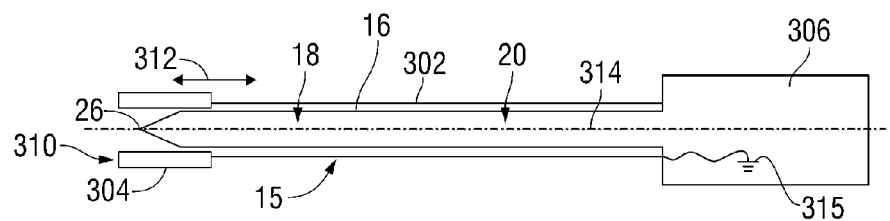
FIG. 3 is a schematic, cross-sectional side view of an ablation probe having a retractable sheath according to some embodiments of the present disclosure.

When the radiating portion 18 is removed from tissue after energy, e.g., microwave energy, is applied to a tissue volume, a shield is placed between the radiating portion 18 and the patient and clinician. As shown in FIG. 3, the shield may include a retractable sheath 302 that surrounds the entire length of the shaft 15 in a fully-extended state. The retractable sheath includes a retractable sheath 302 and a tip cover 304. In some embodiments, the retractable sheath 302 is a compressible plastic cylinder. The tip cover 304 covers the pointed tip 26 to prevent injury. The tip cover 304 may be made of a semi-rigid or rigid material (e.g., a semi-rigid or rigid plastic). The retractable sheath 302 attaches to the handle 320.

In some embodiments, the retractable sheath 302 and/or the tip cover 304 are made of a compressible, electrically conductive material formed in the shape of a cylinder. The compressible, electrically conductive material may be a metal, such as copper. In other embodiments, the retractable sheath 302 and/or the tip cover 304 are coated on their inner and/or outer surfaces with a compressible, electrically conductive material. The retractable sheath 302 and/or the tip cover 304 may be electrically coupled to electrical ground 315 to form an electromagnetic enclosure, which contains the electromagnetic fields generated by the radiating portion 18 to prevent radiation into the environment.

Figure 4:
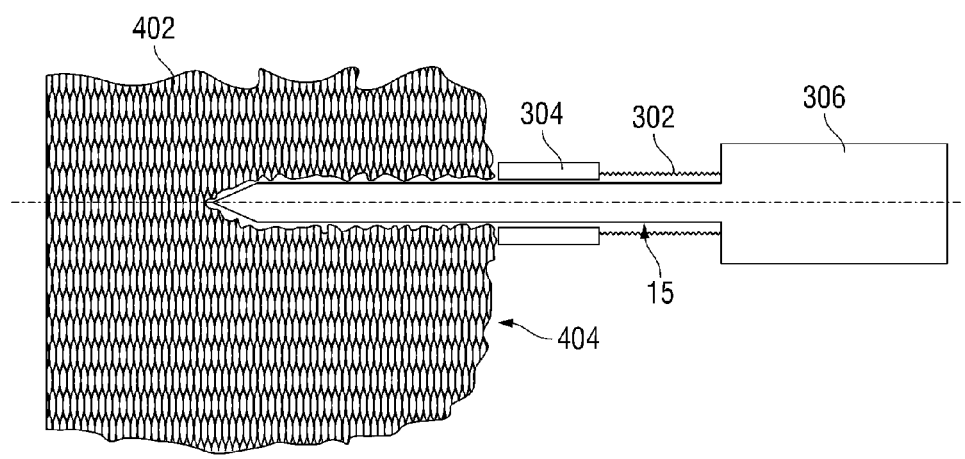
FIG. 4 is a schematic, cross-sectional side view of the ablation probe of FIG. 3 in which the retractable sheath is in a retracted state.

Because the retractable sheath 302 is compressible, the tip cover 304 is movable along a longitudinal axis 314 of the shaft 15. As shown in FIG. 4, when the shaft 15 is inserted in tissue 402, the bottom surface 310 of the tip cover 304 mates with the outside surface 404 of a target volume of the tissue 402, which pushes the tip cover 304 towards the handle 320 and compresses the retractable sheath 302. When the shaft 15 is removed from tissue 402, the tip cover 304 and the retractable sheath 302 decompress and extend to cover the entire length of the shaft 15.

Figure 5A:
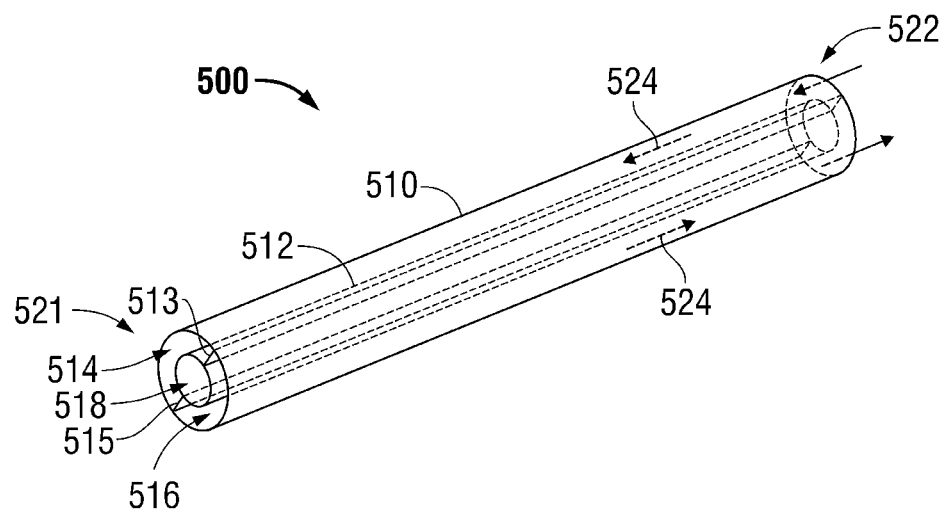
FIG. 5A is a schematic, perspective view of a retractable sheath according to other embodiments of the present disclosure.

FIG. 5A shows a retractable sheath 500 having fluid conduits 514, 516. A cooling fluid 524, 526 having appropriate dielectric properties flows through the fluid conduits 514, 516 to form a fluid shield around the radiating portion 18 of the shaft 15. The fluid conduits 514, 516 are formed between the inner surface of the outer wall 510 and the outer surface of the inner wall 512. Multiple conduits may be formed in the retractable sheath 500 by forming conduit walls 513, 515 that extend between the inner surface of the outer wall 510 and the outer surface of the inner wall 512. The conduit wall 513 forms a first fluid conduit 514 and the conduit wall 515 forms a second fluid conduit 516. In other embodiments, more than two conduit walls may be formed in the retractable sheath 500 to provide more than two fluid conduits.

Figure 5B:
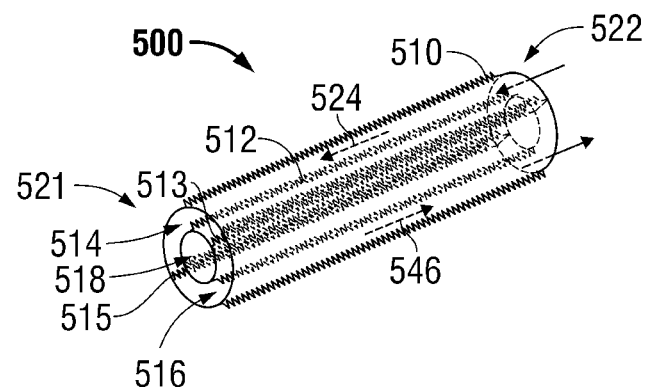
FIG. 5B is a schematic, perspective view of the retractable sheath of FIG. 5A in a retracted state.

The conduit walls 513, 515 shown in FIGS. 5A and 5B have a linear shape along the length of the retractable sheath 500. In other embodiments, however, the conduit walls 513, 515 may have a non-linear shape, such as a curved shape.

As shown in FIG. 5A, the fluid conduit 514 may carry a cooling fluid 524 to the distal end 521 of the retractable sheath 500 and the fluid conduit 516 may carry the cooling fluid 524 to the proximal end of the retractable sheath 500. The retractable sheath 500 may include a tip cover (not shown) at the distal end 521 of the retractable sheath 500 that directs the cooling fluid 524 flowing in the fluid conduit 514 to the fluid conduit 516. In this manner, the cooling fluid 524 may be circulated through the retractable sheath 500.

As illustrated in FIG. 5B, when the shaft 15 is placed within tissue, the retractable sheath 500 compresses to a retracted state. When the shaft 15 is removed from the tissue, the fluid pump 34 supplies a cooling fluid 524 to the retractable sheath 500 under a working pressure sufficient to extend the retractable sheath 500 to the extended state shown in FIG. 5A.

In some embodiments, the metal-coated retractable sheath of FIGS. 3 and 4 is combined with the retractable sheath 500 of FIGS. 5A and 5B. For example, the retractable sheath 500 may be coated with a metal or any other electrically conductive material.

Figure 6:
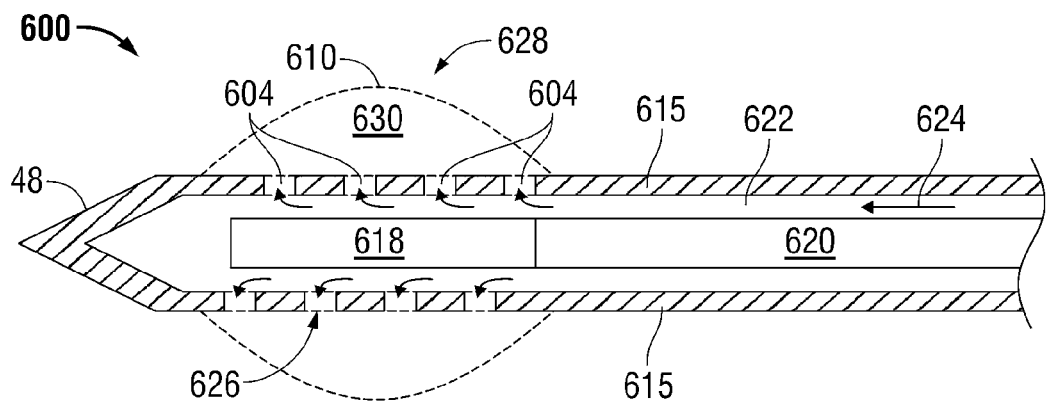
FIG. 6 is a schematic, cross-sectional side view of an ablation probe incorporating an expandable balloon according to some embodiments of the present disclosure.

FIG. 6 shows a cross-sectional side view of an ablation probe 600, e.g., a microwave ablation probe, having an expandable balloon 610. The shaft 615 is a hollow elongated shaft or introducer having a wall 616 that encloses an electrical conductor having an antenna 618, e.g., a microwave antenna, and a coaxial cable 620. The coaxial cable 620 is electrically coupled to the antenna 618 and supplies energy, e.g., microwave energy, to the antenna 618. The space between the inner surface of the wall 616 and the outer surfaces of the antenna 618 and the coaxial cable 620 forms a fluid conduit 622 through which cooling fluid flows to cool the antenna 618.

The ablation probe 600 also includes multiple apertures 604 formed in the wall 616 of the shaft 615. The apertures 604 are formed around the shaft 15 along the length of the antenna 618. Alternatively, the apertures 604 are formed around the shaft 15 along a portion of the length of the antenna 618 or near the antenna 618. The expandable balloon 610 is disposed on the outer surface of the wall 616 and is configured to cover the apertures 604.

When the ablation probe 600 is placed in tissue and is transferring energy to the tissue, the balloon 610 maintains a normal state 626 in contact with or in close proximity to the outer surface of the wall 616. When the ablation probe 600 is removed from the tissue, the fluid conduit 622 carries a shielding fluid 624, which may be a pressurized fluid, to the apertures 604. The shielding fluid 624 flows through the apertures 604 and expands the balloon 610 to an expanded state 628. In the expanded state 628, the balloon 610 defines and holds a volume 630 of shielding fluid 624 around the antenna 618. The volume 630 of shielding fluid 624 absorbs and attenuates the energy radiating from the antenna 618 before the energy can radiate into the environment.

In some embodiments, the ablation probe 600 interfaces with the fluid pump 34 of FIG. 1 that is configured to supply a cooling fluid to the ablation probe 600 at a pressure level sufficient to maintain the balloon 610 in an expanded state 628 when the ablation probe 600 is outside of tissue. But, when the ablation probe 600 is inserted into tissue, the tissue compresses the balloon 610 against the outer surface of the shaft 615 to bring the balloon 610 back to its normal state 626. When the ablation probe 600 is removed from tissue, the pressure of the cooling fluid expands the balloon 610 to an expanded state 628 and forms a large volume of fluid around the antenna 618 to absorb most of the electromagnetic energy radiating from the antenna 618.

Figure 7A:
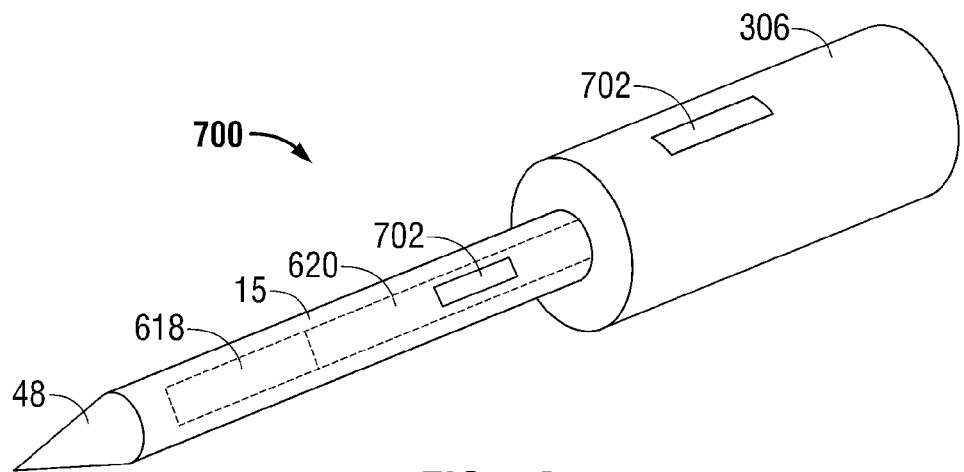
FIG. 7A is a schematic, perspective view of an ablation probe having a passive thermal sensor according to some embodiments of the present disclosure.

FIG. 7A is a perspective view of an ablation probe 700 having a temperature indicator 702 (e.g., a passive temperature indicator) disposed on the outer surface of the handle 306. The temperature indicator 702 may optionally be disposed on the outer surface of the shaft 15. The temperature indicator 702 is a device that displays the temperature of the handle 306 or the shaft 15. For example, the temperature indicator 702 may include a material that varies in color or brightness as the temperature of the handle 306 or the shaft 15 varies. In particular, the brightness of the material may increase as the temperature of the handle 306 or the shaft 15 increases.

Figure 7B:
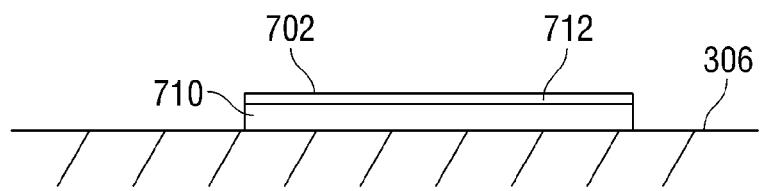
FIG. 7B is a schematic, cross-sectional side view of the passive thermal sensor disposed on the ablation probe of FIG. 7A.

FIG. 7B illustrates an embodiment of the temperature indicator 702. The temperature indicator 702 includes a layer of thermal gel 710, e.g., a gel pad, disposed on the surface of the handle 308 and thermal paper 712 disposed on the layer of thermal gel 710. The layer of thermal gel 710 may attach to the handle 308 (or the shaft 15) through a thermally conductive adhesive.

As described above, the thermal paper 712 may change color to indicate a change in temperature of the handle 308 or shaft 15 to which the temperature indicator 702 is attached. Thus, when the ablation probe 700 is removed from tissue, any energy radiating from the antenna 618 heats the shaft 15 and the handle 308 through thermal conduction. The heat in the handle 308 then transfers through the layer of thermal gel 710 to the thermal paper 712 and changes the color of the thermal paper 712. The changed color of the thermal paper 712 indicates to the clinician that the temperature of the handle 308 exceeds a predetermined level.

In some embodiments, the temperature indicator 702 is disposed on the handle 306 of an ablation probe that also includes the retractable sheath 302 of FIGS. 3 and 4. In other embodiments, the temperature indicator 702 is disposed on the retractable sheath 302 of FIGS. 3 and 4 in case the retractable sheath 302 absorbs heat from the radiating portion 18 of the shaft 15 and heats up.

Figure 8A:
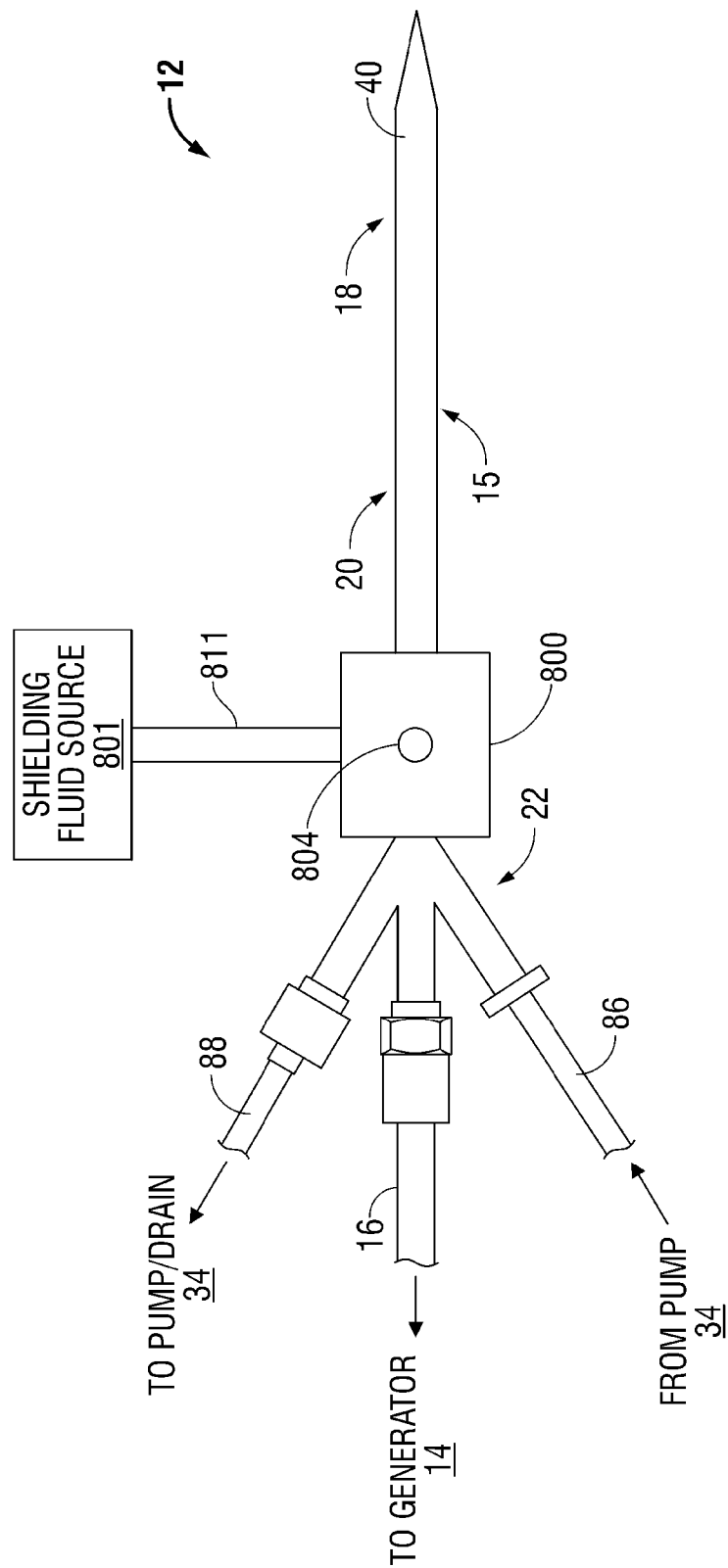
FIG. 8A is a diagram of an ablation probe incorporating a fluid circuit for feeding shielding fluid to the ablation probe.

In some embodiments, the ablation probe 12 is reconfigured to feed a shielding fluid to the radiating portion 18 of the shaft 15 in order to reduce or eliminate radiation from the shaft 15 into the environment. As illustrated in FIG. 8A, the ablation probe 12 includes a fluid circuit module 800 that is fluidly coupled to a shielding fluid source 801 via a second fluid supply conduit 811. As described in greater detail below, the fluid circuit module 800 receives shielding fluid from the shielding fluid source 801 and supplies it to the radiating portion of the shaft 15 when the shaft 15 is removed from tissue after an ablation procedure is completed.

The fluid circuit module 800 includes a button 804 that allows a user of the ablation probe 12 to control the supply of shielding fluid to the radiating portion 18 of the shaft 15. For example, the fluid circuit module 800 may be configured (1) to supply the cooling fluid to the radiating portion 18 of the shaft 15 when the user depresses the button 804 and (2) to supply a mixture of the cooling fluid and the shielding fluid to the radiating portion 18 of the shaft 15 when the user releases the button 804. Alternatively, the fluid circuit module 800 may be configured (1) to supply the cooling fluid to the radiating portion 18 of the shaft 15 when the user depresses the button 804 a first time and (2) to supply a mixture of the cooling fluid and the shielding fluid to the radiating portion 18 of the shaft 15 when the user depresses the button 804 a second time.

Figure 8B:
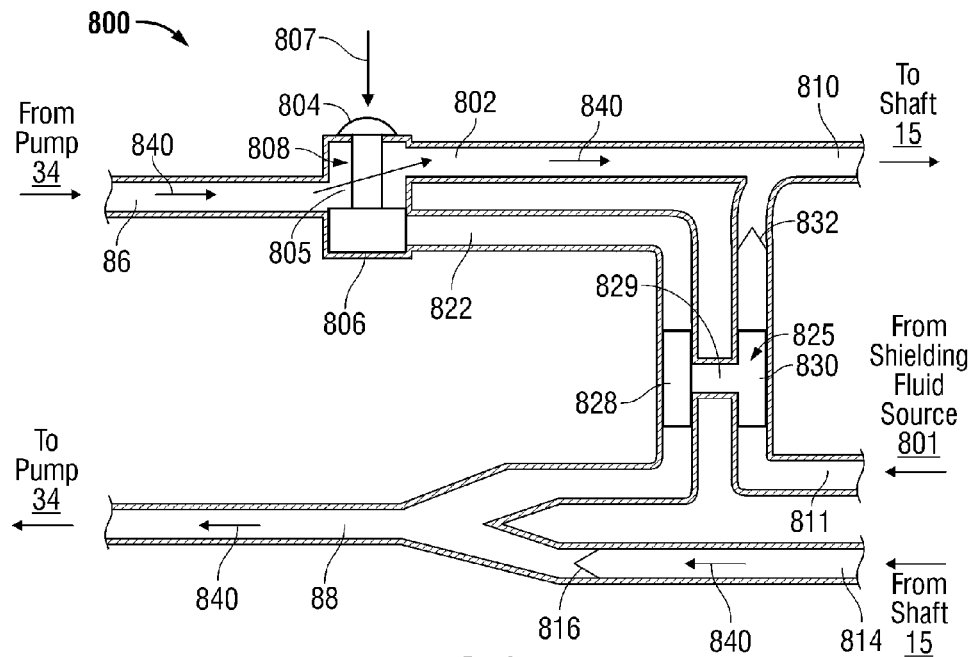
FIGS. 8B and 8C are schematic diagrams of a fluid circuit for adjusting the properties of the shielding fluid fed to the ablation probe according to some embodiments of the present disclosure.
Figure 8C:
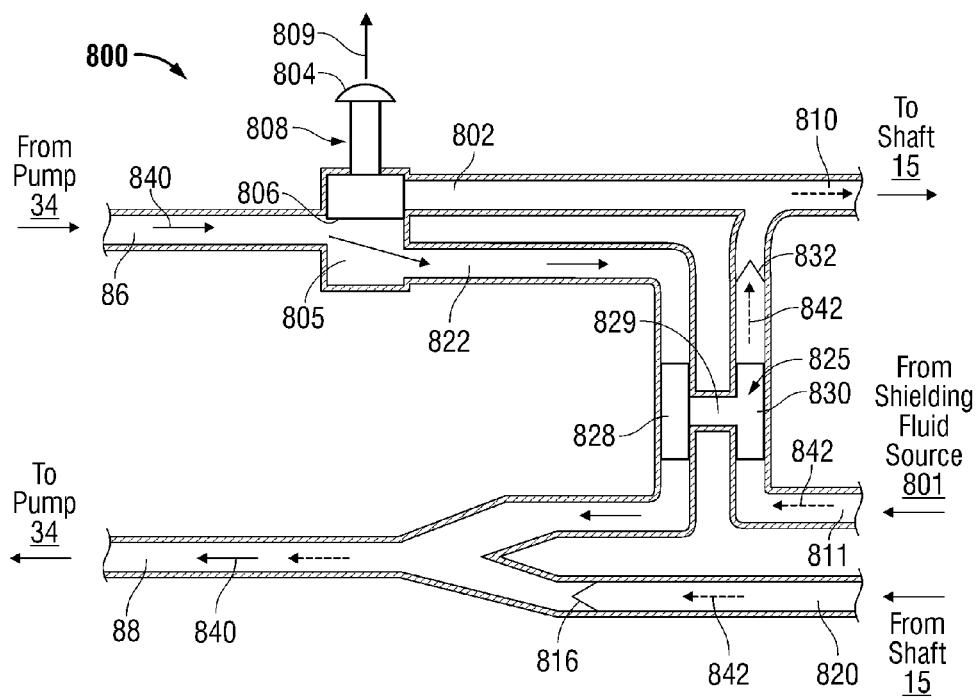

FIGS. 8B and 8C are schematic diagrams of an embodiment of the fluid circuit module 800 of FIG. 8A. FIGS. 8B and 8C illustrate the operation of an embodiment of the fluid circuit module 800 that allows a user to select whether to supply a cooling fluid or a mixture of the cooling fluid and a shielding fluid to the radiating portion 18 of the shaft 15 of the ablation probe 12. As shown in FIG. 8A, the fluid circuit 800 includes the fluid supply conduit 86 (hereinafter referred to as the first fluid supply conduit 86) fluidly coupled between the fluid pump 34 of FIG. 1 and a common fluid supply conduit 810. The common fluid supply conduit 810, in turn, is in fluid communication with the shaft 15.

The fluid circuit 800 also includes a bypass fluid conduit 822 that is fluidly coupled to the first fluid supply conduit 86 through a bypass fluid chamber 805. The flow of fluid through the bypass fluid conduit 822 is controlled by a bypass valve assembly 808. The bypass valve assembly 808 includes a piston 806 that is movable in a vertical direction within the bypass fluid chamber 805. The bypass valve assembly 808 also includes a button 804 or other similar manual control mechanism coupled to the piston 806 that allows a user to move the piston 806 within the bypass fluid chamber 805.

In operation, when a user depresses the button 804 to move the piston 806 to the bottom of the bypass fluid chamber 805, a first fluid 840 supplied by the fluid pump 34 flows through the first fluid supply conduit 86, the bypass fluid chamber 805, and the common fluid supply conduit 810 to the shaft 15. The first fluid 840, however, does not enter the bypass fluid conduit 822 because the piston 806 covers the inlet of the bypass fluid conduit 822. The common fluid supply conduit 810 supplies the first fluid 840 to the shaft to facilitate the radiation of microwave energy from the radiating portion of the conductor disposed within the shaft 15. The fluid circuit 800 also includes a fluid return line 88 that carries the first fluid 840 returned from the shaft 15 to the fluid pump 34.

As shown in FIG. 8B, the fluid circuit 800 also includes the second fluid supply conduit 811, which supplies a second fluid 842 (e.g., a shielding fluid or a cooling fluid) to the common fluid conduit 810. The common fluid conduit 810 delivers the second fluid 842 to the shaft to minimize or prevent radiation of electromagnetic energy from the radiating portion of the shaft 15 to tissue or the surrounding environment. The second fluid 842 may be any fluid that absorbs the electromagnetic energy radiating from the antenna. For example, the second fluid 842 may be a liquid solution containing particles that absorb electromagnetic energy radiating from the antenna.

To pump the second fluid 842 through the second fluid supply conduit 811, the fluid circuit 800 incorporates a second fluid pump assembly 825. The second fluid pump assembly 825 includes a fluid pump 830 and an impeller 828 coupled to the fluid pump 830. As shown in FIG. 8B, the fluid pump 830 is positioned within the second fluid supply conduit 811. The impeller 828 is operatively coupled to the fluid pump 830 through a shaft 829. The impeller 828 is positioned within the bypass fluid conduit 822 so that the first fluid 840 flowing through the bypass fluid conduit 822 causes the impeller to rotate and drive the fluid pump 830. In other embodiments, the second fluid pump assembly 825 may include different components that use the flow of the first fluid 840 flowing through the bypass fluid conduit 822 to cause the second fluid 842 to flow in the second fluid supply conduit 811.

The second fluid supply conduit 811 also includes a check valve 832 that allows the second fluid to flow in one direction from a second fluid source (not shown) to the common fluid conduit 810. The check valve also prevents any first fluid 840 flowing in the first fluid supply conduit 86 from entering the second fluid supply conduit 811. In some embodiments, the check valve 832 is a duck bill valve.

When the user desires to apply microwave energy to tissue, the user depresses the button 804 with his/her finger to cause the first fluid 840 to flow through the common fluid supply conduit 810 to the radiating portion of the shaft 15. As described above, the first fluid 840 increases the efficiency of the radiating portion of the microwave conductor disposed within the shaft 15. When the user desires to stop applying microwave energy to tissue, the user removes his/her finger from the button 804 or depresses the button 804 a second time to cause the second fluid 842 to flow through the common fluid supply conduit 810 to the shaft 15 to shield the radiating portion of the microwave conductor. For example, the bypass valve assembly 808 may be spring loaded so that the bypass valve assembly 808 returns to the up position 809 when the user removes pressure from the button 804.

In the up position 809, the piston 806 prevents the first fluid 840 from flowing to the common fluid supply conduit 810 and directs the first fluid 840 into the bypass fluid conduit 822. The first fluid 840 flows through the impeller 828 causing it to rotate and drive the fluid pump 830 through the shaft 829 of the fluid pump assembly 825. Then, the fluid pump 830 pumps the second fluid 842 from a second fluid source (not shown) through the check valve 832 to the common fluid supply conduit 810. The first fluid 840 flows out of the bypass fluid conduit 822 and into the fluid return conduit 820, which carries the first fluid 840 to the fluid pump 34. The second fluid 842 flows to the shaft 15 via the common fluid supply conduit 810 and then returns from the shaft 15 via the fluid return conduit 820. The second fluid 842 mixes with the first fluid 840 and returns to the fluid pump 34.

Figure 9A:
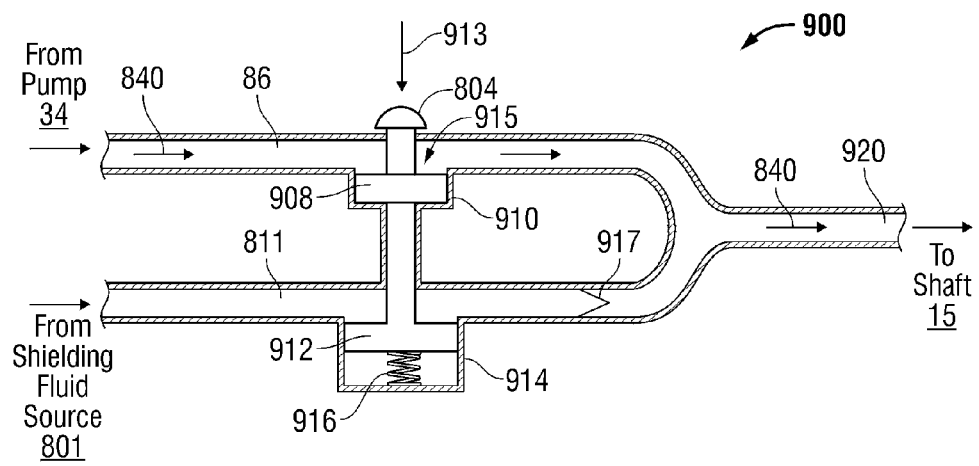
FIGS. 9A and 9B are schematic diagrams of a fluid circuit for adjusting the properties of the fluid fed to the ablation probe according to other embodiments of the present disclosure.
Figure 9B:
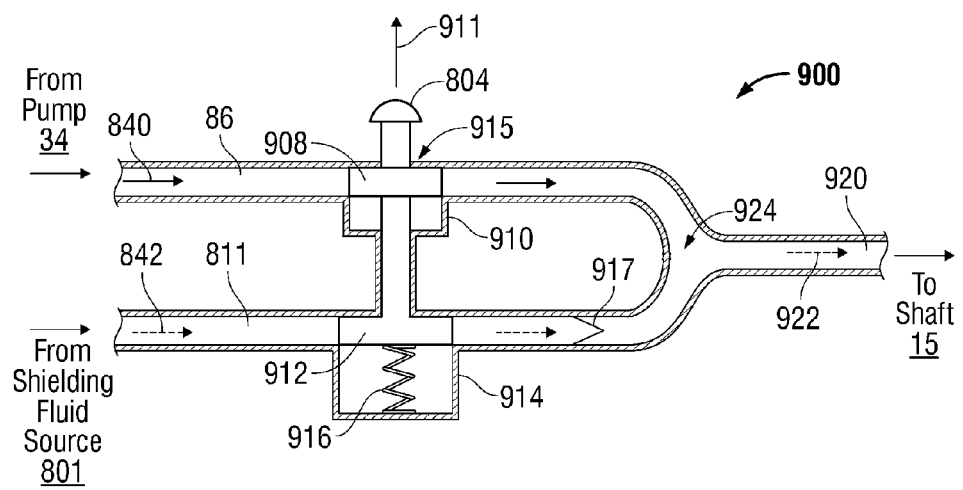

FIGS. 9A and 9B show another embodiment of a fluid circuit 900 that allows the user to select whether to supply a cooling fluid or a mixture of a cooling fluid and another fluid to the shaft 15. Similar to the embodiment of FIGS. 8B and 8C, the fluid circuit 900 includes a first fluid supply conduit 86 and a second fluid supply conduit 904 that feed into a common fluid supply conduit 920. Unlike the embodiment of FIGS. 8B and 8C, however, the first fluid supply conduit 86 includes a first recessed portion 910 and the second fluid supply conduit 811 includes a second recessed portion 914. The first recessed portion 910 is shaped and dimensioned to receive an impeller 908 and the second recessed portion 914 is shaped and dimensioned to receive a fluid pump 912. As in the embodiment FIGS. 8B and 8C, the impeller 908 and fluid pump 912 are operatively coupled to each other and form a portion of a fluid valve assembly 915.

The fluid valve assembly 915 also includes a button 906 or other control mechanism that is coupled to the impeller 908. The first fluid supply conduit 86 includes a first recessed portion 910 and the second fluid supply conduit 904 includes a second recessed portion 914. The fluid valve assembly 915 can move between an up position and a down position 913 within the first and second recessed portions 910, 914. The fluid valve assembly 915 is spring loaded with a spring 916 that is positioned between the bottom surface of the second recessed portion 914 and the bottom surface of the second fluid pump 912 to maintain the fluid valve assembly 915 in the up position 911. Other types and arrangements of springs could also be used to maintain the fluid valve assembly 915 in the up position 911.

As shown in FIG. 9A, if the button 906 is depressed, a first fluid 940 flows through the first fluid supply conduit 86 to the common fluid supply conduit 920, while no fluid flows through the second fluid supply conduit 904. This is because the impeller 908 is positioned in the first recessed portion 910 away from the flow of the first fluid 940 so that the first fluid 940 cannot cause the impeller 908 to rotate and drive the second fluid pump 912. Also, the second fluid pump 912 is positioned in the second recessed portion 914 so that the second fluid pump 912 cannot draw the second fluid 942 through the second fluid supply conduit 904.

As shown in FIG. 9B, when the button 905 is released, the impeller 908 moves into the flow of the first fluid 940 and the second fluid pump 912 moves into the flow path of the second fluid 942. The flow of the first fluid 940 causes the impeller 908 to rotate. The impeller 908, in turn, drives the second fluid pump 912. In operation, the second fluid pump 912 draws the second fluid 942 through the second fluid supply conduit 904 and into a mixing area 924 where the first fluid 940 flowing through the impeller 908 mixes with the second fluid 942 to form a third fluid 922. The fluid valve assembly 915 may include gears that control the speed of the second fluid pump 912 and thus the flow rate of the second fluid 942 to control the ratio of first fluid 940 to second fluid 942 in the third fluid 922. In this manner, the properties of the third fluid 922 may be adjusted to improve its ability to shield the radiating portion of the ablation probe from nearby tissue or the external environment.

In some embodiments, the first fluid 940 is a water-based buffer solution and the second fluid 942 is air or a similar gas, such as nitrogen, which agitates the water-based buffer solution when the button 905 is released. The air and buffer solution mixture may have different dielectric properties than the buffer solution alone. These different dielectric properties would hinder unnecessary energy transfer from the radiating portion of the shaft or probe into the environment.

The structures and methods described above for reducing or eliminating energy that radiates from ablation probes into the environment may be used in any combination to achieve varying levels of shielding. For example, an ablation system may incorporate the apertures 604 and the balloon 610 of FIG. 6, and the fluid circuit module 800 of FIGS. 8A-8C. In such an ablation system, the fluid circuit module 800 supplies shielding fluid to the balloon 610 through the apertures 604 when a user removes his/her finger from the button 804 at the completion of an ablation procedure. The shielding fluid is supplied to the balloon 610 at a pressure level sufficient to expand the balloon 610 when the ablation probe is removed from the tissue.

In another example, an ablation system may incorporate the retractable sheath 500 of FIGS. 5A-5B (i.e., the retractable sheath having fluid conduits) and the fluid circuit 900 of FIGS. 9A-9B. In such an ablation system, a mixture of shielding fluid and cooling fluid is supplied to the retractable sheath 500 when a user removes his/her finger from the button 804 at the completion of an ablation procedure. In yet another example, an ablation system may incorporate the temperature indicator 702 of FIGS. 7A and 7B and the fluid circuit 800 of FIGS. 8A-8C.

While several embodiments of the disclosure have been shown in the drawings and/or discussed herein, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An ablation system, comprising:
   an ablation probe including:
      a shaft having a proximal portion and a distal portion, the distal portion including an antenna configured to deliver energy to tissue; and
      a retractable sheath surrounding at least a radiating portion of the shaft, the retractable sheath including a rigid tip cover disposed at a distal portion of the retractable sheath, a first fluid conduit configured to deliver a cooling fluid to the distal portion of the shaft, and a second fluid conduit configured to return the cooling fluid to the proximal portion of the shaft;
   a fluid source in fluid communication with the first fluid conduit;
   a fluid pump in fluid communication with the fluid source, the fluid pump configured to pump a fluid through the first fluid conduit; and
   a generator electrically coupled to the antenna, the generator configured to supply electrical energy to the antenna.

2. The ablation system according to claim 1, which further comprises a fluid disposed in the fluid source, wherein the fluid has dielectric properties that reduce the energy radiating from the radiating portion of the shaft.

3. The ablation system according to claim 1, which further comprises a fluid disposed in the fluid source, wherein the fluid is selected from the group consisting of air, a mixture of cooling fluid and air, and a mixture of cooling fluid and a dielectric material.

4. The ablation system according to claim 1, wherein the energy is microwave energy.

5. The ablation system according to claim 1, wherein the retractable sheath is configured to retract when the shaft is inserted in tissue.

6. The ablation system according to claim 5, wherein the fluid pump is configured to supply a fluid to the first fluid conduit under a working pressure sufficient to extend the retractable sheath as the shaft is removed from tissue.

7. The ablation system according to claim 1, wherein the retractable sheath is configured to prevent at least a portion of the energy from radiating outside of the retractable sheath.

8. The ablation system according to claim 5, wherein the distal portion of the shaft includes a sharp tip, the rigid tip cover configured to enclose the sharp tip when the retractable sheath is in an extended state.

9. The ablation system according to claim 5, further comprising a handle coupled to a proximal portion of the shaft, the retractable sheath coupled to a distal portion of the handle.

10. The ablation system according to claim 5, wherein the retractable sheath is a compressible plastic cylinder configured to compress when the shaft is inserted in tissue and at least a portion of the compressible plastic cylinder is coated with an electrically conductive material.

11. The ablation system according to claim 5, wherein the retractable sheath is electrically coupled to an electrical ground.

12. The ablation system according to claim 5, wherein the retractable sheath is a compressible, electrically conductive material formed in the shape of a cylinder and configured to compress when the shaft is inserted in tissue.

13. The ablation system according to claim 12, wherein the compressible, electrically conductive material is a metal.

14. The ablation system according to claim 13, wherein the metal is copper.

15. The ablation system according to claim 5, wherein the retractable sheath includes an inner wall and an outer wall, and wherein the first fluid conduit is disposed between the inner and outer wall.

16. The ablation system according to claim 15, wherein the outer wall of the retractable sheath is coated with an electrically conductive material.

* * * * *